US012644621B2

(12) United States Patent
Mou et al.

(10) Patent No.: US 12,644,621 B2
(45) Date of Patent: Jun. 2, 2026

(54) SYSTEM FOR DETECTING AND CLEANING INDOOR AIR POLLUTION

(71) Applicant: MICROJET TECHNOLOGY CO., LTD., Hsinchu City (TW)

(72) Inventors: Hao-Jan Mou, Hsinchu City (TW); Chin-Chuan Wu, Hsinchu City (TW); Yung-Lung Han, Hsinchu City (TW); Chi-Feng Huang, Hsinchu City (TW)

(73) Assignee: MICROJET TECHNOLOGY CO., LTD., Hsinchu City (TW)

( * ) Notice: Subject to any disclaimer, the term of this patent is extended or adjusted under 35 U.S.C. 154(b) by 725 days.

(21) Appl. No.: 18/156,078

(22) Filed: Jan. 18, 2023

(65) Prior Publication Data

US 2024/0151421 A1 May 9, 2024

(30) Foreign Application Priority Data

Nov. 9, 2022 (TW) .................................. 111142864

(51) Int. Cl.
*F24F 11/64* (2018.01)
*A61L 9/014* (2006.01)
(Continued)

(52) U.S. Cl.
CPC .............. *F24F 11/64* (2018.01); *A61L 9/014* (2013.01); *A61L 9/18* (2013.01); *B01D 46/0045* (2013.01); *B01D 46/442* (2013.01); *B01D 46/46* (2013.01); *B01D 53/885* (2013.01); *F24F 3/16* (2013.01); *F24F 13/28* (2013.01); *A61L 2209/111* (2013.01); *A61L 2209/12* (2013.01); *A61L 2209/14* (2013.01); *A61L 2209/16* (2013.01); *A61L 2209/22* (2013.01); *B01D 2255/802* (2013.01); *B01D*

*2273/30* (2013.01); *B01D 2279/50* (2013.01); *F24F 2011/0002* (2013.01); *F24F 2110/52* (2018.01);
(Continued)

(58) Field of Classification Search
CPC ........ F24F 11/64; F24F 13/16; F24F 2110/64; A51L 9/014; A51L 9/18; B01D 46/0045; B01D 46/442; B01D 46/46; B01D 53/885
USPC ......................................................... 454/187
See application file for complete search history.

(56) References Cited

U.S. PATENT DOCUMENTS 11,649,977 B2 * 5/2023 He ........................... F24F 11/63
700/276
2020/0224915 A1 * 7/2020 Nourbakhsh ............ F24F 11/54

FOREIGN PATENT DOCUMENTS

CN 112413789 A 2/2021
TW I722793 B 3/2021
(Continued)

*Primary Examiner* — Avinash A Savani
*Assistant Examiner* — Dana K Tighe
(74) *Attorney, Agent, or Firm* — Birch, Stewart, Kolasch & Birch, LLP

(57) ABSTRACT

A system for detecting and cleaning indoor air pollution adapted to be utilized in an indoor space with an HVAC system includes one or more outdoor gas detection devices, a plurality of channels, a plurality of indoor gas detection devices, a plurality of physical-typed or chemical-typed filtering devices, and a control central processor. The blower of the filtering device receives a control command so as to be driven and to generate an air convection which is directed. Therefore, the air pollution is filtered by the filtering component to allow the indoor air pollution data to approach to almost zero, so that a gas in the indoor space is cleaned to a safe and breathable state.

23 Claims, 26 Drawing Sheets

(51) Int. Cl.

| | |
|---|---|
| *A61L 9/18* | (2006.01) |
| *B01D 46/00* | (2022.01) |
| *B01D 46/44* | (2006.01) |
| *B01D 46/46* | (2006.01) |
| *B01D 53/88* | (2006.01) |
| *F24F 3/16* | (2021.01) |
| *F24F 13/28* | (2006.01) |
| *F24F 11/00* | (2018.01) |
| *F24F 110/52* | (2018.01) |
| *F24F 110/64* | (2018.01) |
| *F24F 110/65* | (2018.01) |
| *F24F 110/66* | (2018.01) |
| *F24F 110/70* | (2018.01) |
| *G01N 15/075* | (2024.01) |

(52) U.S. Cl.
CPC ....... *F24F 2110/64* (2018.01); *F24F 2110/65* (2018.01); *F24F 2110/66* (2018.01); *F24F 2110/70* (2018.01); *G01N 15/075* (2024.01)

(56)                     References Cited

FOREIGN PATENT DOCUMENTS

| TW | 202235847 | A | 9/2022 |
|---|---|---|---|
| TW | I778474 | B | 9/2022 |
| TW | 202242320 | A | 11/2022 |

* cited by examiner

B1

SYSTEM FOR DETECTING AND CLEANING INDOOR AIR POLLUTION

CROSS-REFERENCE TO RELATED APPLICATION

This non-provisional application claims priority under 35 U.S.C. § 119(a) to Patent Application No. 111142864 filed in Taiwan, R.O.C. on Nov. 9, 2022, the entire contents of which are hereby incorporated by reference.

BACKGROUND

Technical Field

The present invention relates to a system for detecting and cleaning indoor air pollution, in particular, to a system adapted to be utilized in an indoor space with a heating, ventilation and air conditioning system (hereinafter, abbreviated as HVAC system), therefore the air pollution can be filtered and cleaned quickly, allowing the indoor air pollution data of the indoor space to approach to almost zero (a non-detection state) and allow the gas (air) of the indoor space to a safe and breathable state.

Related Art

In light of people paying more and more attention to the ambient air quality in daily life, it is noted that the particulate matters (PM1, PM2.5, PM10) around the air including carbon dioxide, total volatile organic compounds (TVOC), formaldehyde and even particulates, aerogels, bacteria, viruses contained in the air might affect the human health, even might be life-threatening when exposure to these gases.

However, currently, it is not easy to control the indoor air quality since the affecting factors of the indoor air quality include not only the outdoor space air quality but also the air conditioning and the pollution sources in the indoor space (especially the dusts originated from poor circulation of air in the indoor space). Therefore, the heating and cooling air conditioners or air cleaners are utilized for improving the indoor air quality.

Consequently, for intelligently and quickly detect the indoor air pollution source, thereby effectively removing the air pollution from the indoor space, making the air into a safe and breathable state while the air quality in the indoor space is lowering to a default standard, and to monitor the air quality of the indoor space whenever and wherever possible. Hence, it is one of issue to be solved for one or some embodiments of the present invention. Accordingly, it is an issue for one or some embodiments of the present invention to generate an air convection intelligently, to detect the air pollution quickly, to locate the air pollution location, to control a plurality of filtering devices effectively for performing an intelligent computation and to generate an air convection for accelerating the directing of the air pollution, to control the gate to be opened or closed through the control central processor so as to selectively introduce the outdoor air in the indoor space, and to filter and clean the indoor air pollution through the filtering components, so that the air pollution in the indoor space is cleaned to allow the air pollution data to approach to almost zero (a non-detection state), and the air in the indoor space is cleaned to a safe and breathable state.

SUMMARY

One object of the present invention is to propose a system for detecting and cleaning indoor air pollution, adapted to be utilized in an indoor space with an HVAC system, wherein a plurality of gas detection devices is utilized to detect and identify a qualitative property, a concentration, and a location of an air pollution for outputting an air pollution data, wherein a plurality of filtering devices is utilized to filter the air pollution. After the gas detection devices output the air pollution data, an intelligent computation is performed to determine the air pollution location, and the gas detection devices transmit a control command intelligently and selectively to enable a filtering device closest to the air pollution location, guiding the air pollution to the filtering device which is closest to the air pollution location for rapidly filtering. Moreover, the movable filtering device of the filtering devices receives the control command so as to move toward the air pollution location of the indoor space. Moreover, filtering components of the filtering devices are utilized to filter the air pollution at the air pollution location and the air pollution outside the air pollution location which is diffused, moved, and directed by the air convection, accelerating the air pollution to be filtered. Accordingly, the air pollution in the indoor space is filtered to allow the indoor air pollution data of the indoor space to be lowered to the safety detection value in which the air pollution data approaches to a non-detection state, and the air in the indoor space is cleaned to a safe and breathable state. Hence, a performance of locating, guiding, cleaning, and filtering the air pollution can be achieved.

In order to accomplish the above object(s), the present invention proposes a system for detecting and cleaning indoor air pollution adapted to be utilized in an indoor space with an HVAC system, the system includes at least one outdoor gas detection device, a plurality of channels, a plurality of indoor gas detection devices, a plurality of filtering devices, and a control central processor. The at least one outdoor gas detection device is configured to detect a qualitative property and a concentration of an air pollution of an outdoor air and output an outdoor air pollution data. The channels are connected to the indoor space, which further comprises a gate, at least one channel filtering member, and a flow-guiding device, wherein the gate controls the outdoor air to be introduced into the channels, the flow-guiding device guides the outdoor air introduced into the channels to pass through the at least one channel filtering member for filtering, and the flow-guiding device guides the filtered outdoor air into the indoor space. The indoor gas detections devices are configured to detect a qualitative property and a concentration of an air pollution in the indoor space and output an indoor air pollution data. The filtering devices are physical-typed or chemical-typed and disposed in the indoor space, each of the filtering devices includes at least one blower and at least one filtering component. The control central processor is configured to receive the outdoor air pollution data detected by the at least one outdoor gas detection device and the indoor air pollution data detected by the indoor gas detection devices, performing an intelligent computation to locate an air pollution location of the indoor space, and transmit a control command intelligently and selectively. Further, the control central processor is configured to control the gate to be opened or closed and determine whether the outdoor air is introduced into the indoor space through the at least one channel filtering member after the control central processor performs the intelligent computation. The at least one blower of each of the filtering devices is driven by receiving the control command to generate an air convection which is directed, allowing the air pollution in the indoor space to be filtered to allow the indoor air pollution data of the indoor space to be lowered to a safety detection value, in which the air pollution data approaches to a non-detection state, thereby the air in the indoor space is cleaned to a safe and breathable state.

BRIEF DESCRIPTION OF THE DRAWINGS

The invention will become more fully understood from the detailed description given herein below, and the drawings are provided for illustrating the exemplary embodiment only but not the limitation of the invention, wherein.

DETAILED DESCRIPTION

Figure 1:
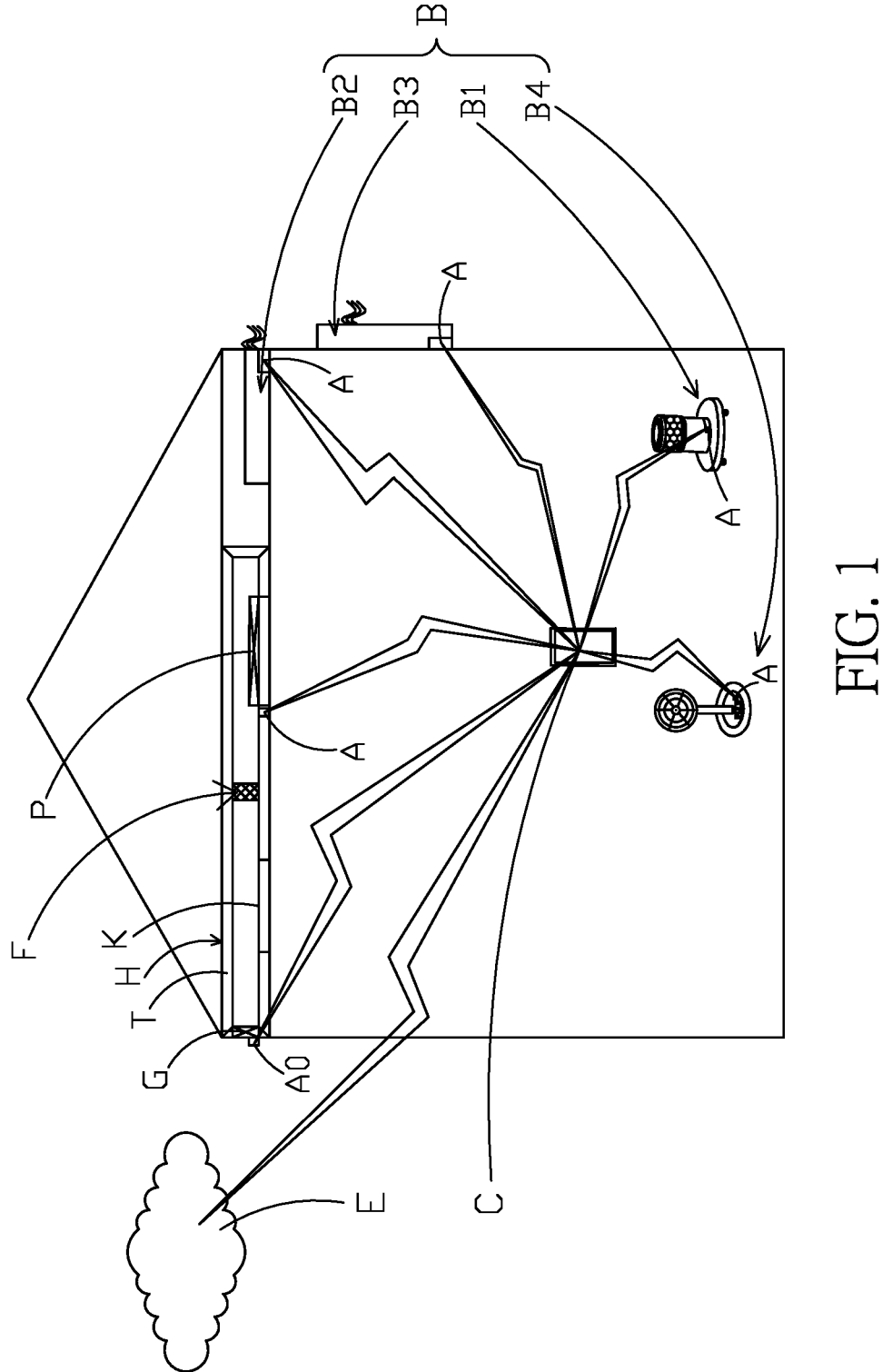
FIG. 1 illustrates a schematic view showing the exemplary embodiment of operation of a system for detecting and cleaning indoor air pollution of an exemplary embodiment in the present invention, wherein the system is utilized in an indoor space.

The present invention will now be described more specifically with reference to the following embodiments. It is to be noted that the following descriptions of different embodiments of this invention are presented herein for purpose of illustration and description only, and it is not intended to limit the scope of the present invention.

Please refer to FIG. 1, FIG. 2A to FIG. 2D, and FIG. 3A to FIG. 3C, according to one or some embodiments of the present invention, a system for detecting and cleaning indoor air pollution (hereinafter, abbreviated as system) adapted to be utilized to a heating, ventilation and air conditioning system (hereinafter, abbreviated as HVAC system) H and an indoor space is provided. The system includes at least one outdoor gas detection device A0, an HVAC system H, a plurality of indoor gas detection devices A, a plurality of filtering devices B, and a control central processor C. The at least one outdoor gas detection device A0 is configured to detect a qualitative property and a concentration of an air pollution of an outdoor air and transmit an outdoor air pollution data. The HVAC system H includes a gate G, at least one channel filtering member F, at least one flow-guiding device P, and a plurality of channels T, wherein each of the channels T is connected to the indoor space. The gate G controls the outdoor air to be introduced into the HVAC system H, moreover, the at least one flow-guiding device P guides the outdoor air introduced into the channels T to pass through the at least one channel filtering member F for filtering, and the at least one flow-guiding device P guides the filtered outdoor air into the indoor space. The indoor gas detection devices A are configured to detect a qualitative property and a concentration of an air pollution in the indoor space and output an indoor air pollution data. The filtering devices B are physical-typed or chemical-typed and are disposed in the indoor space, and each of the filtering devices B includes at least one blower 1 and at least one filtering component 2. The control central processor C is configured to receive the outdoor air pollution data detected by the at least one outdoor gas detection device and the indoor air pollution data detected by the indoor gas detection devices, performing an intelligent computation to locate an air pollution location of the indoor space, and transmit a control command intelligently and selectively. The control central processor C is configured to control the gate G to be opened or closed and determine whether the outdoor air is introduced into the indoor space through the at least one channel filtering member F after the control central processor C performs the intelligent computation. The at least one blower 1 of the filtering devices B is driven by receiving the control command to generate an air convection which is directed, therefore the air pollution in the indoor space is filtered to allow the indoor air pollution data of the indoor space to be a safety detection value, which the air pollution data approaches to a non-detection state, and the gas in the indoor space is cleaned to a safe and breathable state.

It should be noted that, the air pollution (namely the polluted gas) may include at least one selected from the group consisting of particulate matters, carbon monoxide (CO), carbon dioxide ($CO_2$), ozone ($O_3$), sulfur dioxide ($SO_2$), nitrogen dioxide ($NO_2$), lead (Pb), total volatile organic compounds (TVOC), formaldehyde (HCHO), bacteria, fungi, viruses, and any combination thereof. The safety detection value includes a detection value in which the air pollution data approaches to a non-detection state. The safety detection value includes at least one selected from the group consisting of a concentration of PM2.5 which is less than 15 $\mu g/m^3$, a concentration of carbon dioxide which is less than 1000 ppm, a concentration of total volatile organic compounds which is less than 0.56 ppm, a concentration of formaldehyde which is less than 0.08 ppm, a colony-forming unit per cubic meter of bacteria which is less than 1500 $CFU/m^3$, a colony-forming unit per cubic meter of fungi which is less than 1000 $CFU/m^3$, a concentration of sulfur dioxide which is less than 0.075 ppm, a concentration of nitrogen dioxide which is less than 0.1 ppm, a concentration of carbon monoxide which is less than 9 ppm, a concentration of ozone which is less than 0.06 ppm, a concentration of lead which is less than 0.15 $\mu g/m^3$, and/or any combination thereof.

It should be noted that, the flow-guiding device P is a fan. Each of the channels T has a return inlet K adapted to introduce the indoor air in the indoor space back into the channels T to be repeatedly filtered. The at least one channel filtering member F is a high-efficiency particulate air (HEPA) filter, a filter having a minimum efficiency reporting value (MERV) 13 or higher, or any combination thereof.

Figure 2A:
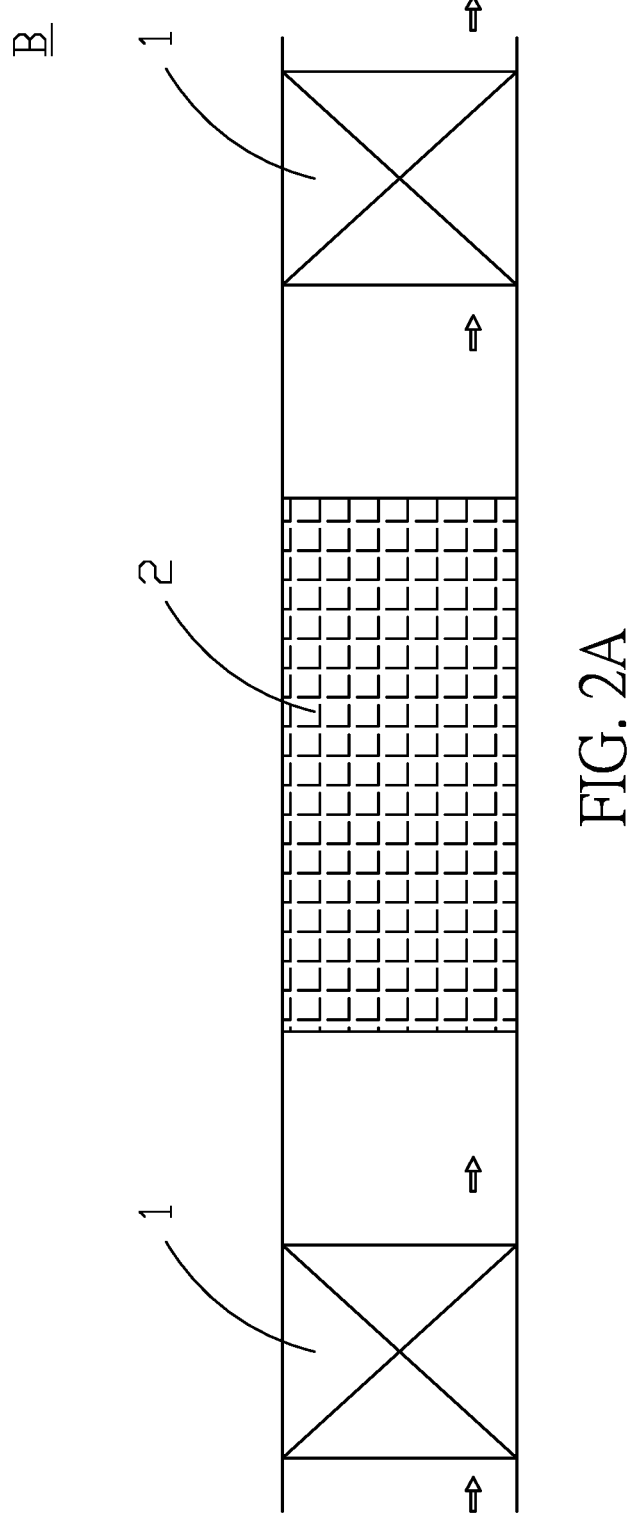
FIG. 2A illustrates a schematic view of a blower and a filtering component of the filtering device in the present invention.
Figure 2B:
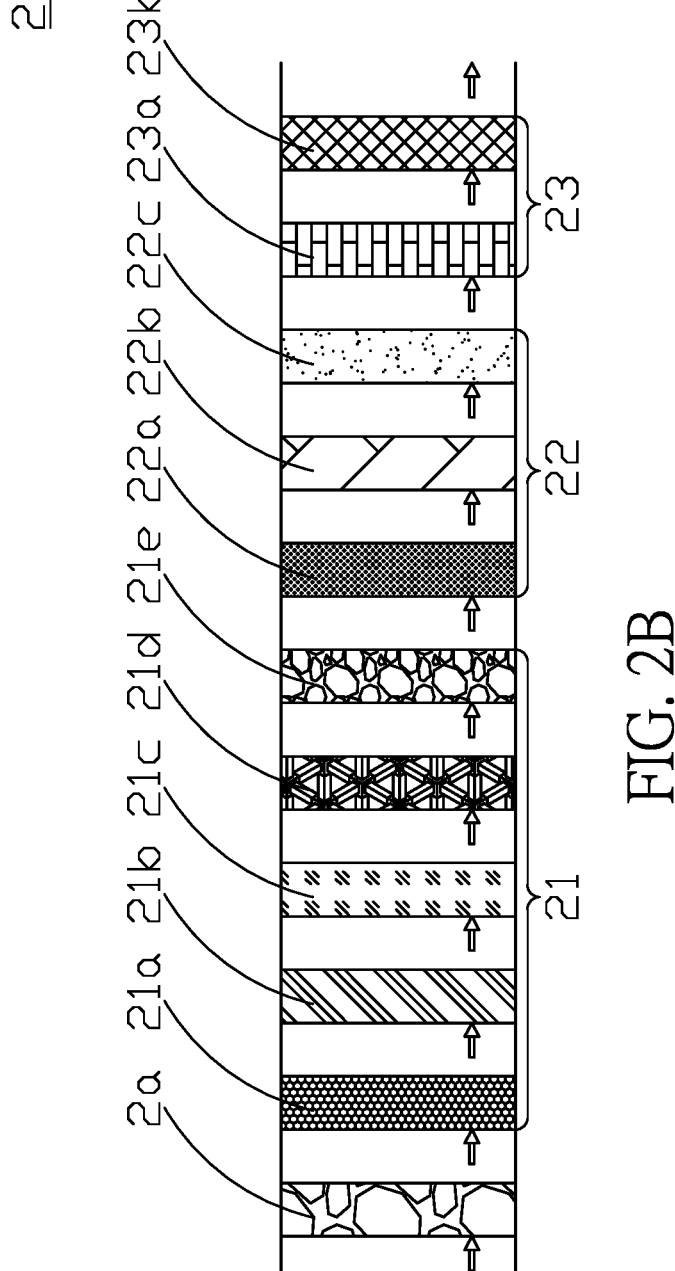
FIG. 2B illustrates a schematic view of the filtering component in the present invention.
Figure 2C:
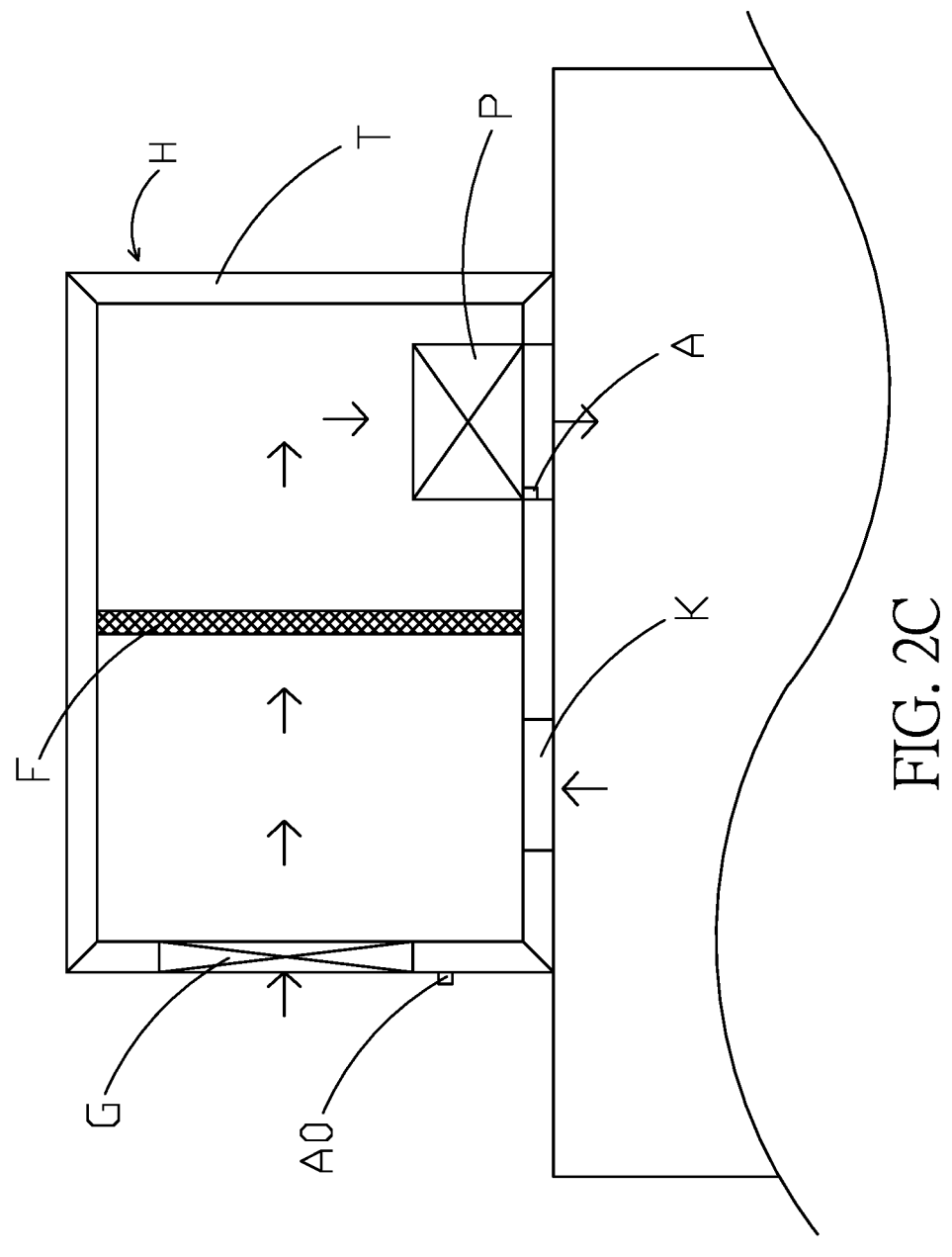
FIG. 2C illustrates a schematic view of a heating, ventilation and air conditioning system in the present invention.
Figure 2D:
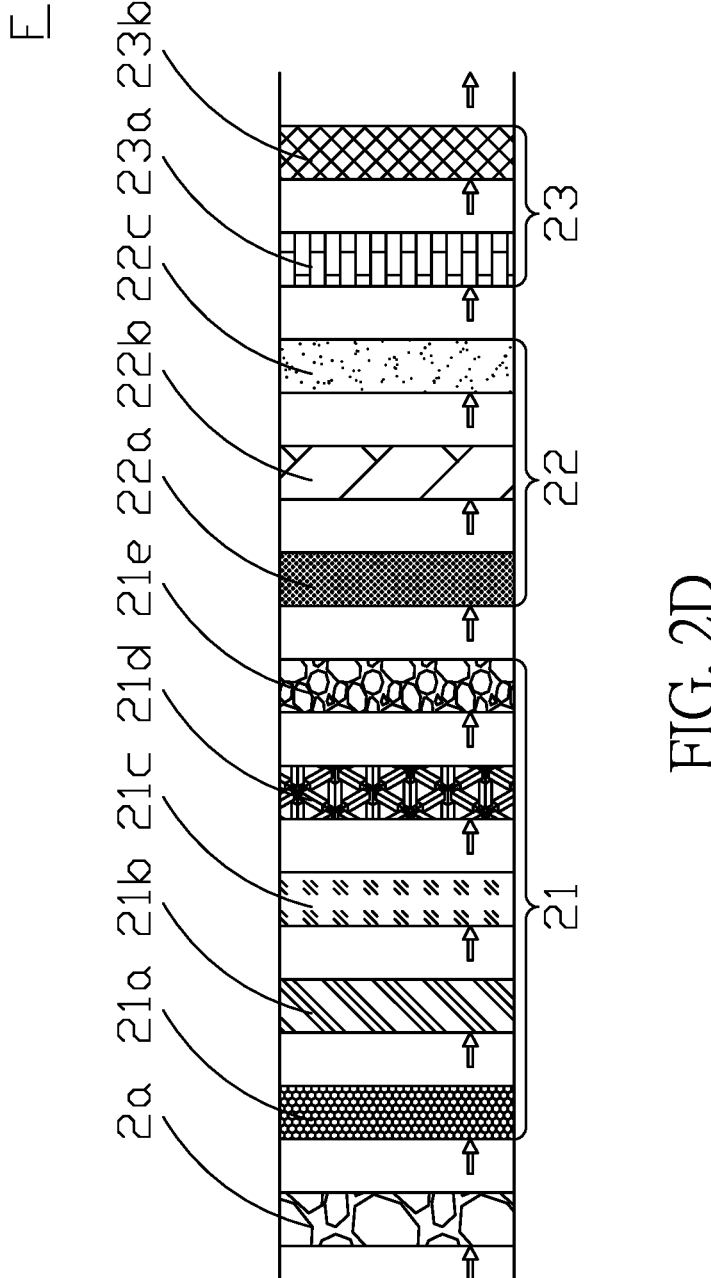
FIG. 2D illustrates a schematic view of a channel filtering member in the present invention.

It should be noted that, as shown in FIG. 2C and FIG. 2D, the system comprises at least one outdoor gas detection device A0 configured to detect the qualitative property and the concentration of the air pollution of the outdoor air, generate an outdoor air pollution data, and output the outdoor air pollution data to the control central processor C (as shown in FIG. 1). The outdoor air flows into the channel T through the gate G by the introduction of the flow-guiding device P, thus the outdoor air is filtered through the channel filtering member F and then flows into the indoor space. After the qualitative property and the concentration of the air pollution in the indoor space are detected by the indoor gas detection device A, an indoor air pollution data is generated and the indoor air pollution data is outputted to the control central processor C. It is worth to note that, the control central processor C is configured to receive the outdoor air pollution data detected by the outdoor gas detection device A0 and the indoor air pollution data detected by the indoor gas detection device A to perform an intelligent computation, wherein the intelligent computation performs the artificial intelligent (AI) computation and big data comparison, transmitting the control command to the filtering device B intelligently and selectively to intelligently control the gate G to be opened or closed. In other words, in some embodiments, if the indoor air quality is better than the outdoor air quality, the control central processor C closes the gate G through the intelligent computation to allow the air in the indoor space to flow back into the return inlet K, therefore, the air flows back to the indoor space through the channel filtering member F and the flow-guiding device P to achieve the indoor air circulation. On the other hand, in some embodiments, if the outdoor air quality is better than the indoor air quality, the control central processor C opens the gate G to allow the outdoor air to be introduced into the indoor space through the channel filtering member F and the flow-guiding device P to achieve the gas exchange of the indoor space.

Furthermore, it is noted that, as shown in FIG. 1 and FIG. 2A to FIG. 2D, the filtering device B may be a movable filtering device B1, a ventilator B2, a cooker hood B3, an electric fan B4, or a combination thereof, but the present invention is not limited thereto. It is understood that, as along as the filtering device B is physical-typed or chemical-typed disposed in the indoor space, and comprises at least one blower 1 and at least one filtering component 2, such apparatus is an extended implementation of the filtering device B, for example, a hair dryer, a vacuum cleaner, an air cleaner, or so on. Each of the indoor gas detection devices A is disposed adjacent to a discharge port of a chamber of a processing channel of a corresponding one of the filtering devices B, thereby each of the indoor gas detection devices A is configured to detect the qualitative property and the concentration of the air pollution of the outdoor air which is filtered by the corresponding one of the filtering devices B and discharged from the processing channel of the corresponding one of the filtering devices B. Take the ventilator B2 as an example, the indoor gas detection device A is disposed at the outlet to detect the qualitative property and concentration of the air pollution of the air.

Figure 3A:
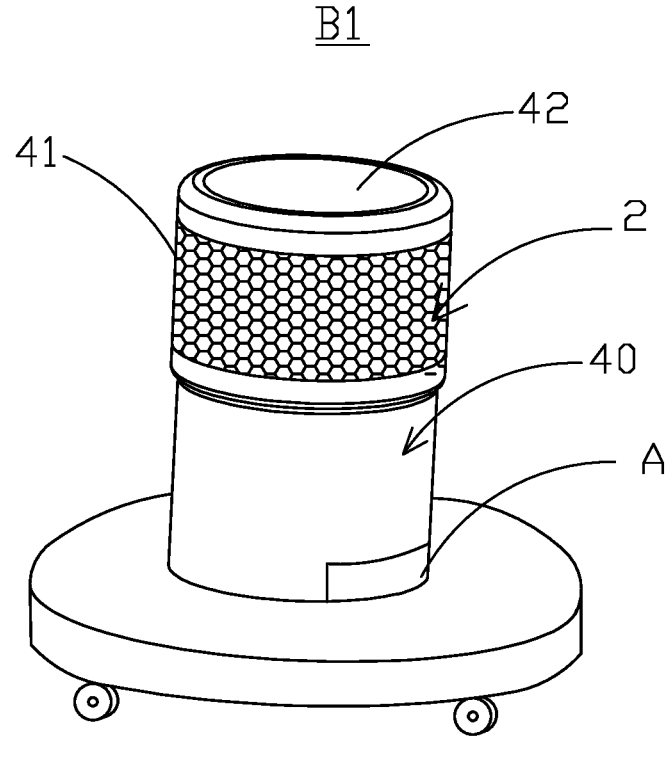
FIG. 3A illustrates a schematic perspective view of a movable filtering device in the present invention.
Figure 3B:
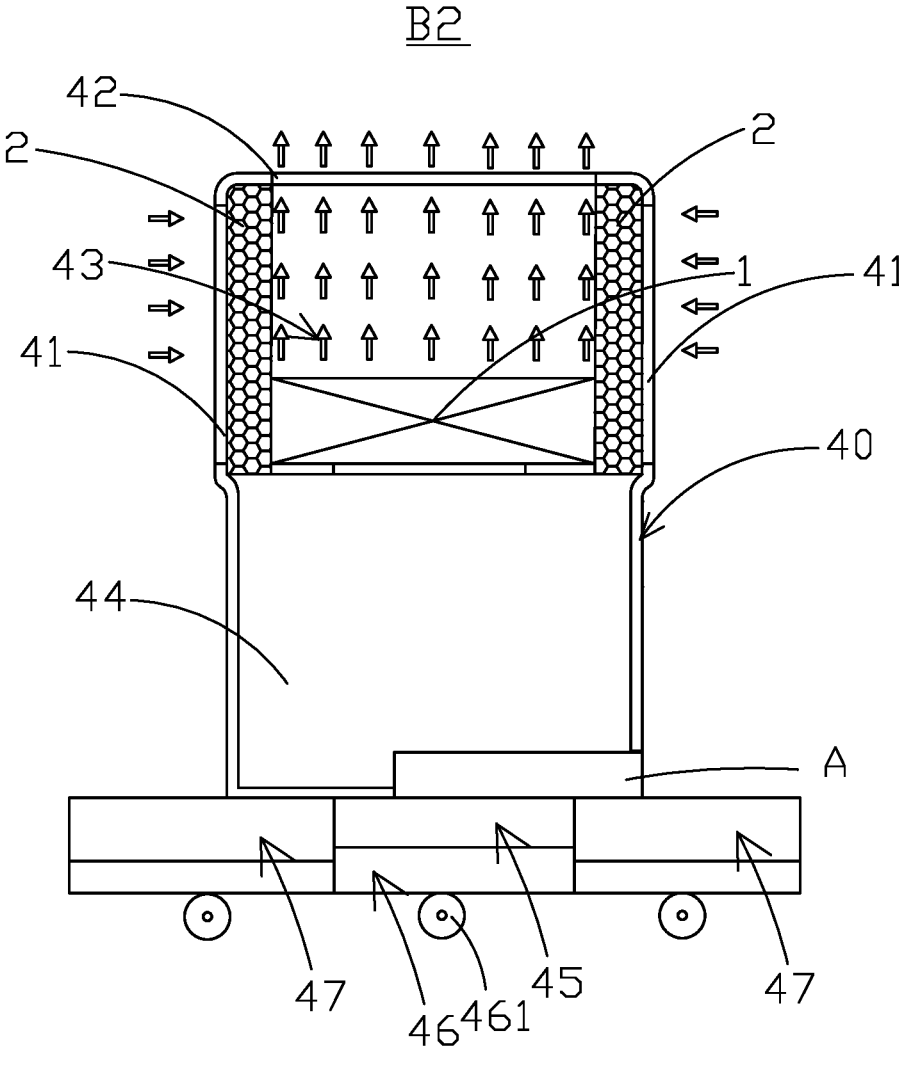
FIG. 3B illustrates a schematic cross-sectional view showing the relative positional relationship among the components of the movable filtering device in the present invention.
Figure 3C:
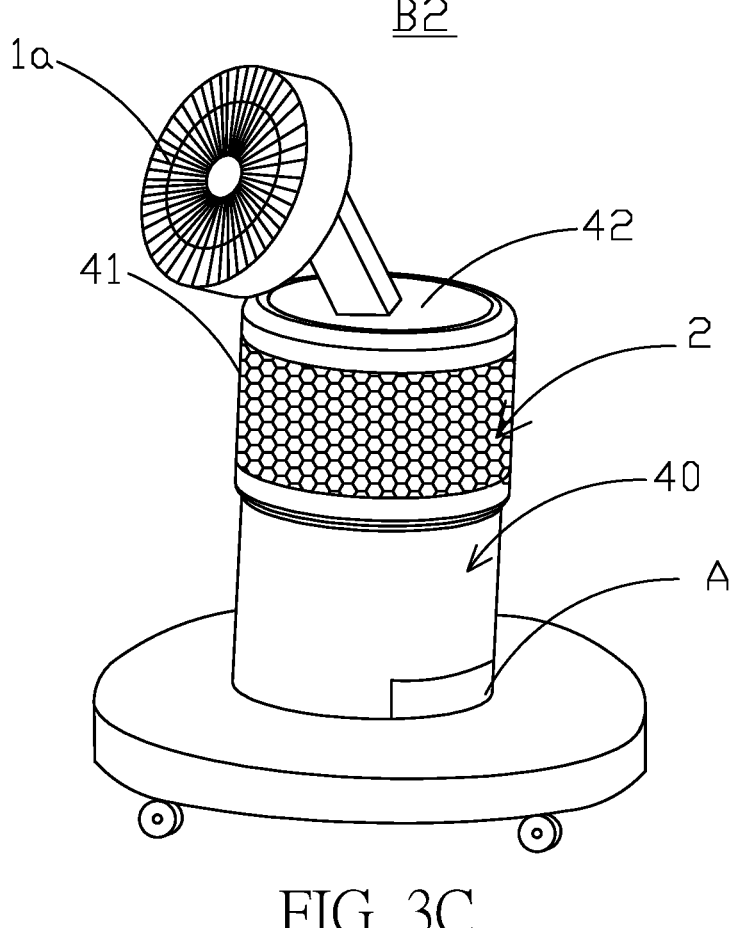
FIG. 3C illustrates a schematic perspective of a view of the movable filtering device utilized along with a directional blower in the present invention.
Figure 4A:
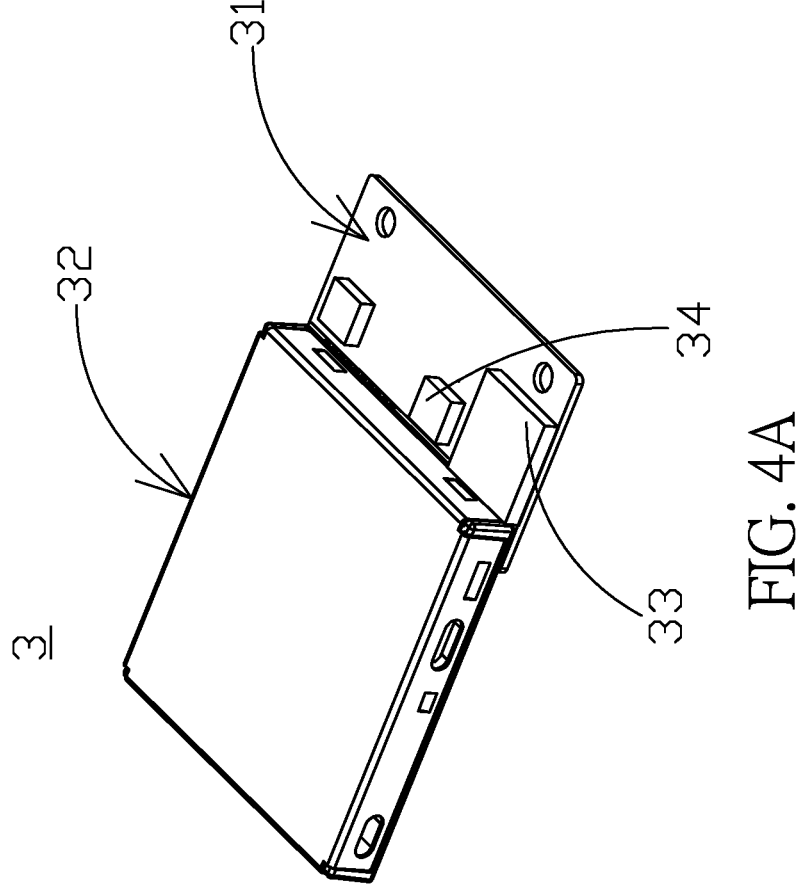
FIG. 4A illustrates a perspective view of a gas detection device in the present invention.
Figure 4B:
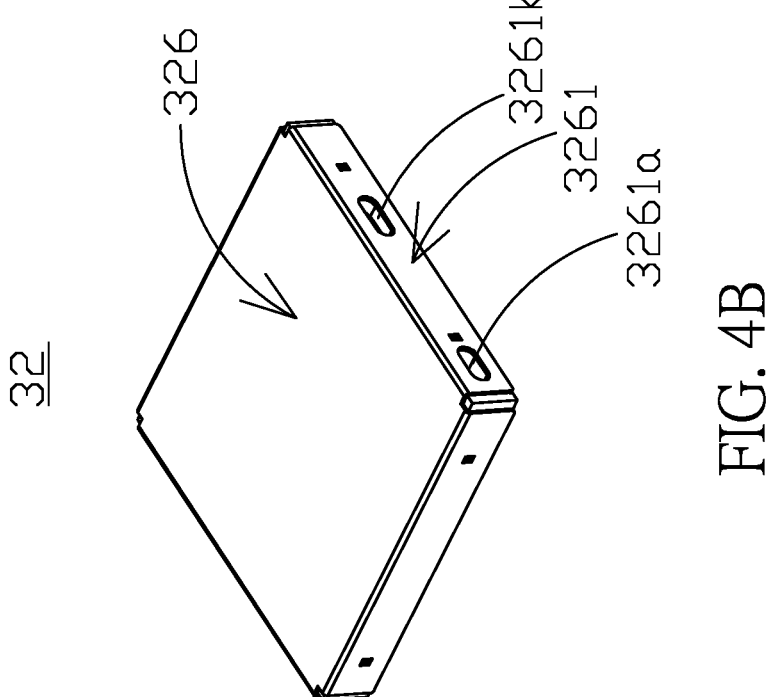
FIG. 4B illustrates a perspective view (1) of a gas detection main body in the present invention.
Figure 4C:
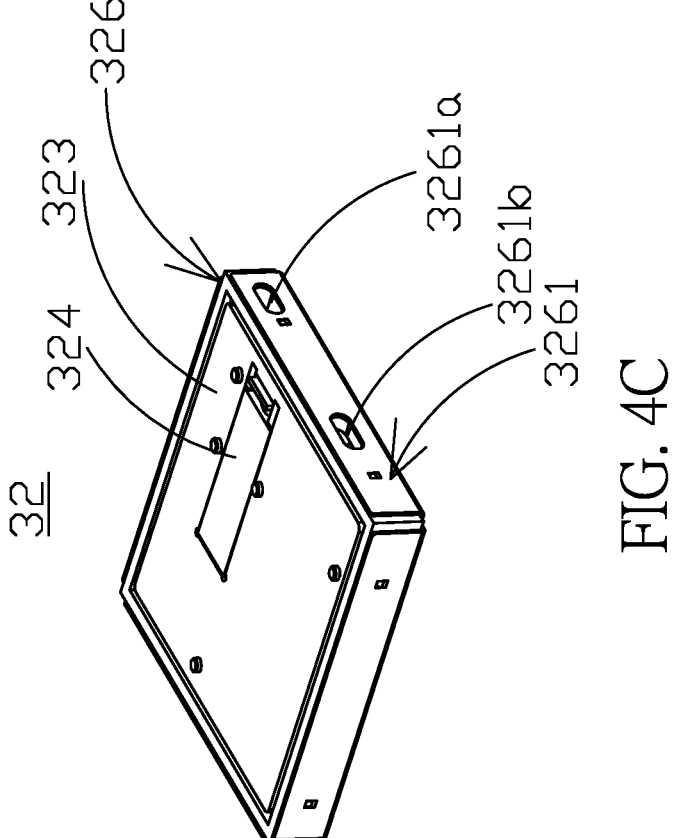
FIG. 4C illustrates a perspective view (2) of the gas detection main body in the present invention.
Figure 4D:
FIG. 4D illustrates a schematic exploded view of the gas detection device in the present invention.
Figure 4D:
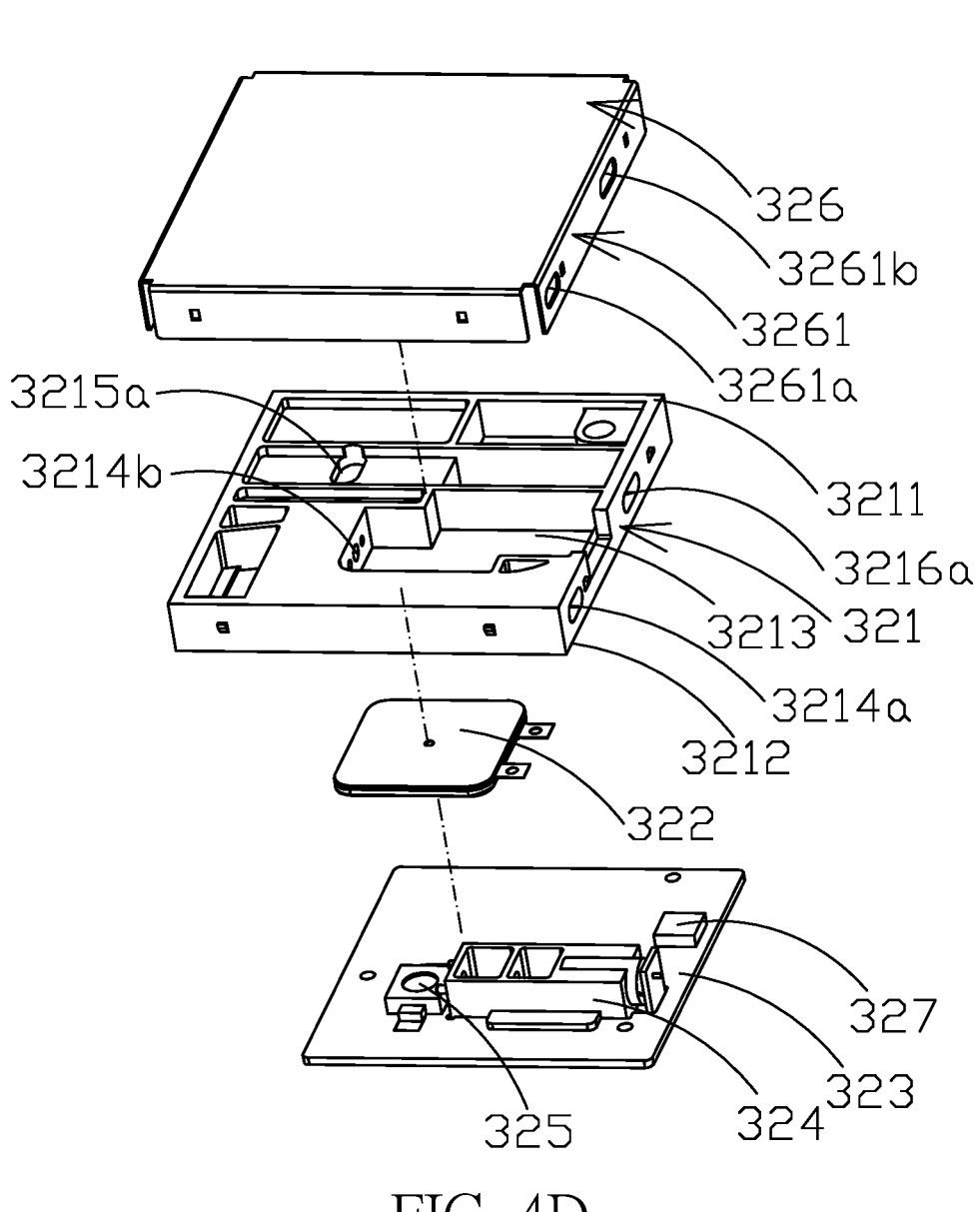
Figure 5A:
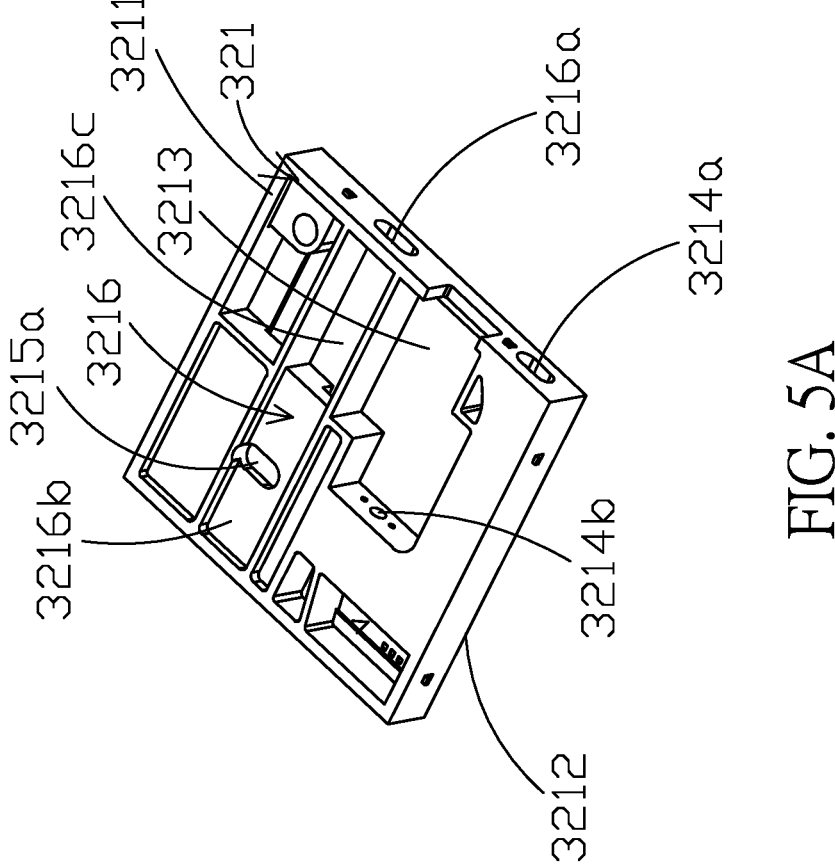
FIG. 5A illustrates a perspective view (1) of a base of the gas detection device in the present invention.
Figure 5B:
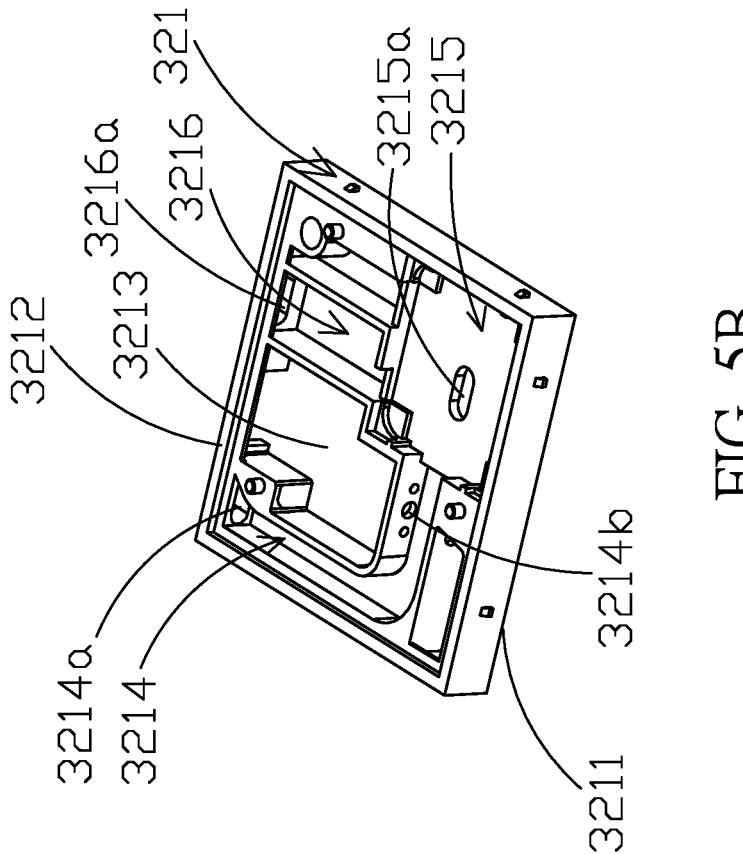
FIG. 5B illustrates a perspective view (2) of the base of the gas detection device in the present invention.
Figure 6:
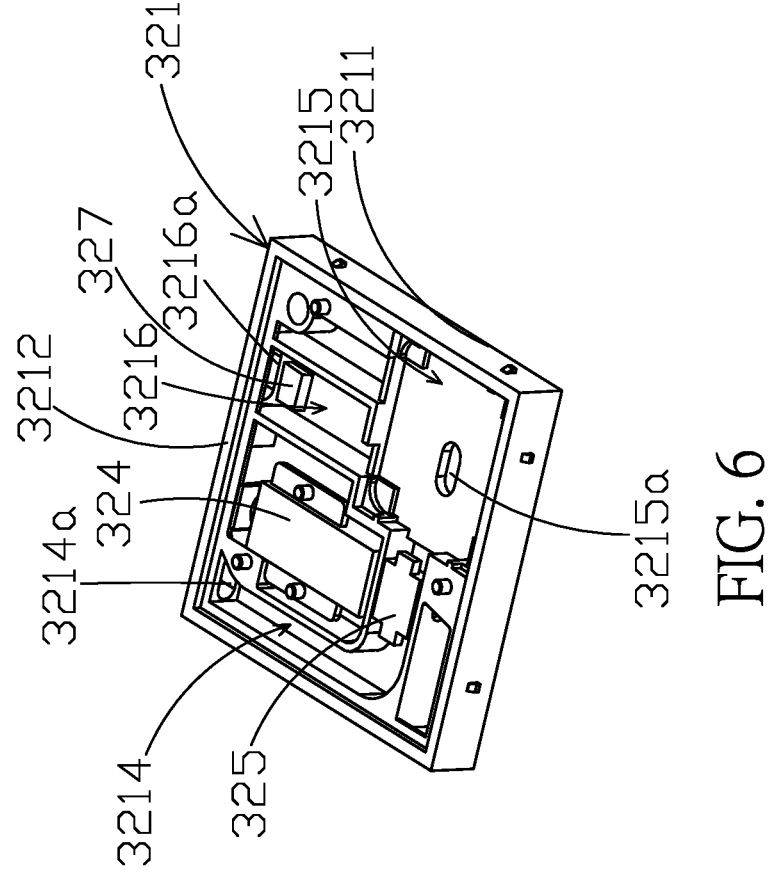
FIG. 6 illustrates a perspective view (3) of the base of the gas detection device in the present invention.
Figure 7A:
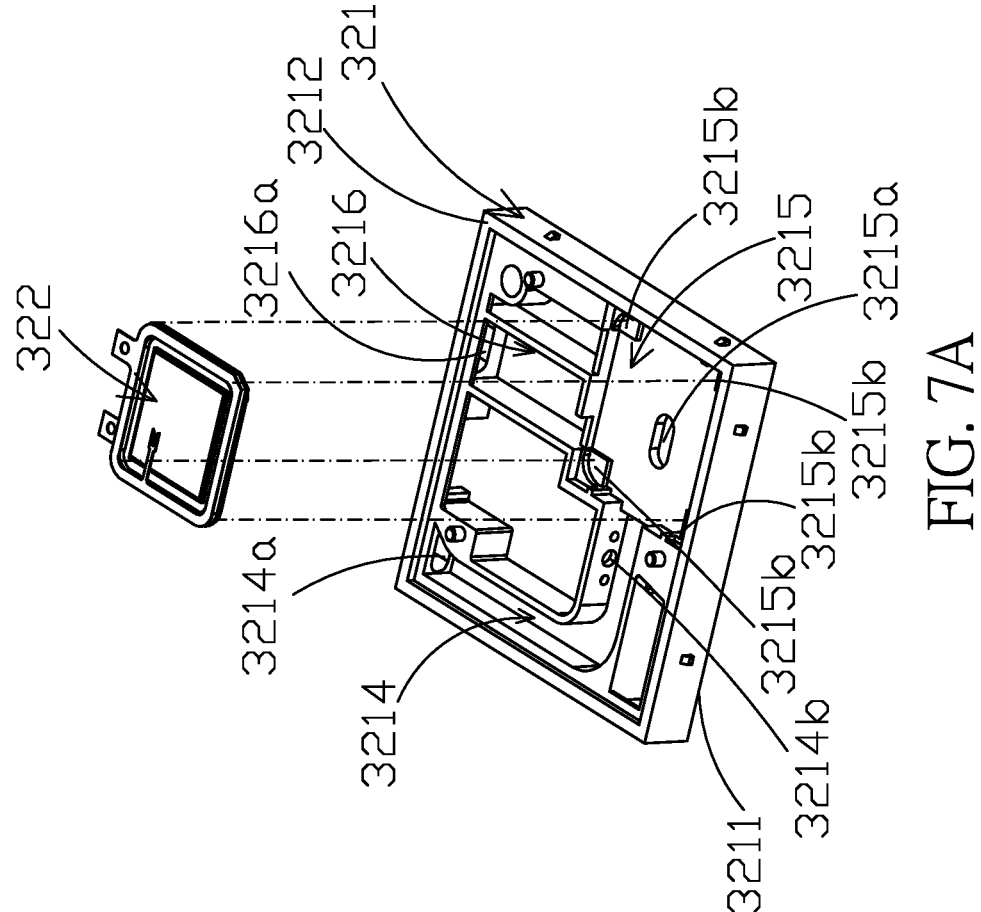
FIG. 7A illustrates an exploded view of a piezoelectric actuator separating from the base of the gas detection device in the present invention.
Figure 7B:
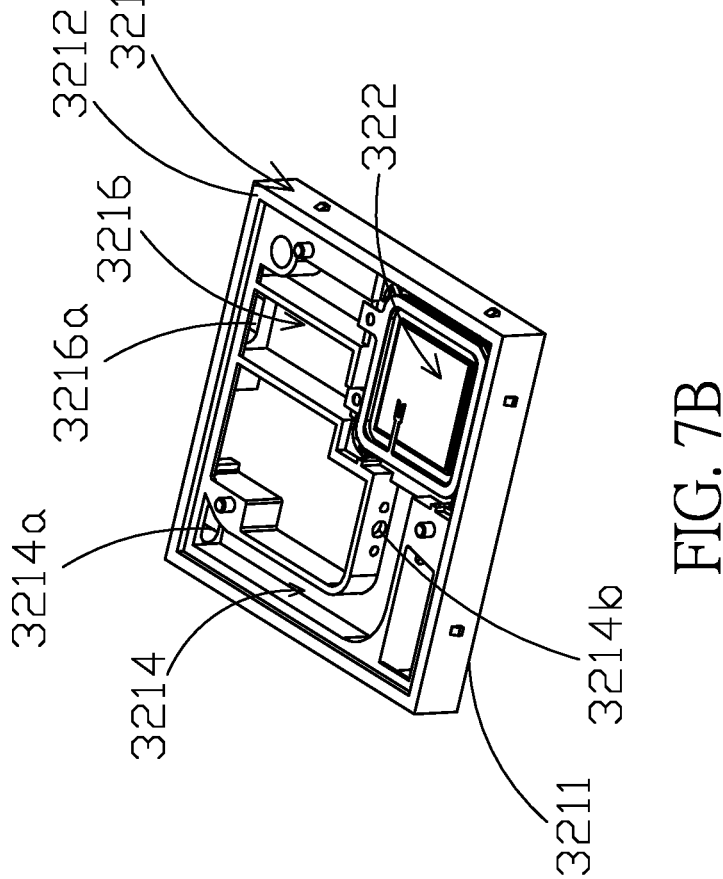
FIG. 7B illustrates a perspective view of the base in combination with the piezoelectric actuator of the gas detection device in the present invention.
Figure 8A:
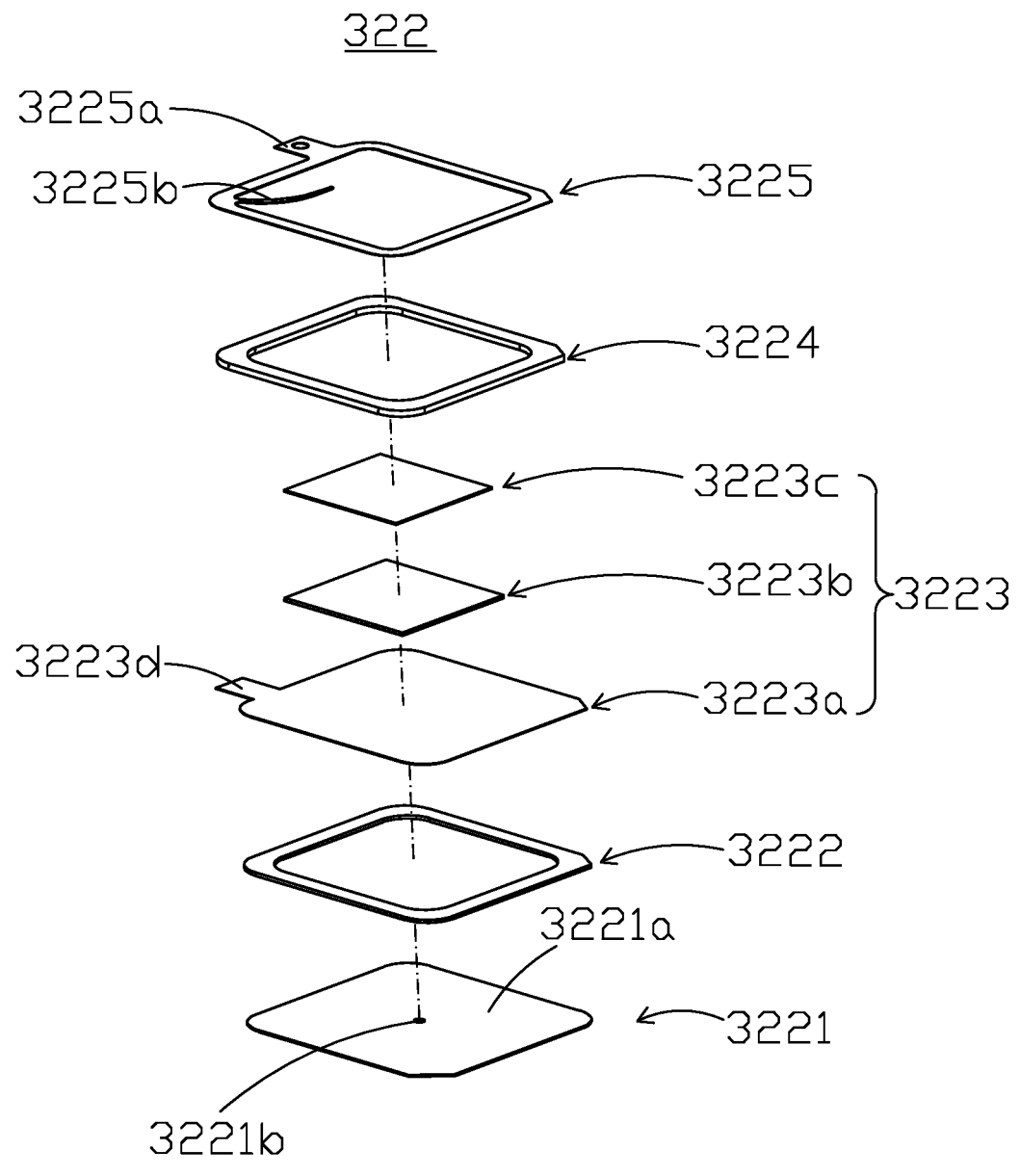
FIG. 8A illustrates an exploded view (1) of the piezoelectric actuator of the gas detection device in the present invention.
Figure 8B:
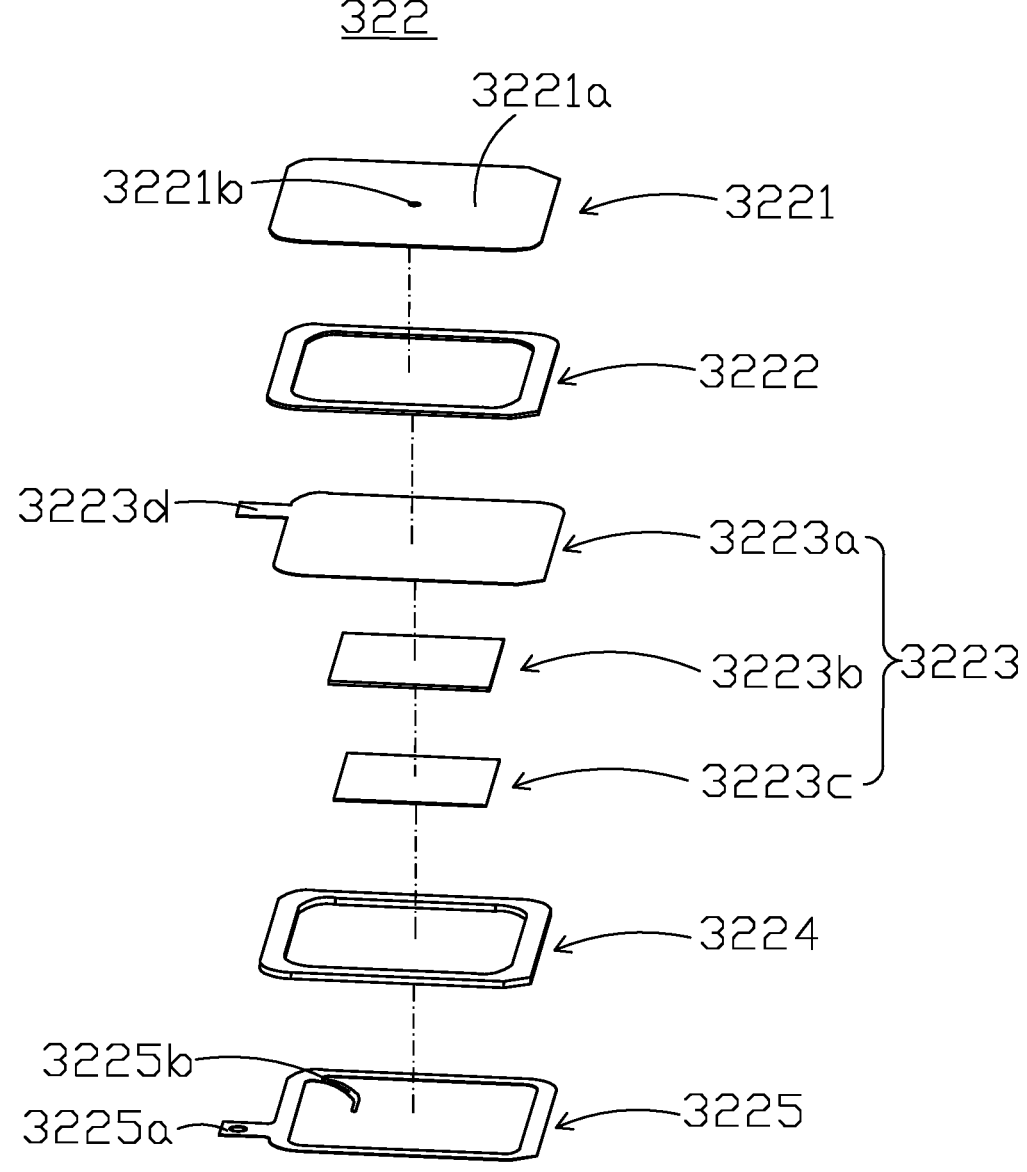
FIG. 8B illustrates an exploded view (2) of the piezoelectric actuator of the gas detection device in the present invention.

Moreover, it is noted that, as shown in FIG. 3A to FIG. 3C, the filtering device B may be a movable filtering device B1. The movable filtering device B1 not only can move within the indoor space to clean the air pollution as shown in FIG. 3A, but also can be a movable filtering device B1 with a directional blower 1a as shown in FIG. 3C. Therefore, the air pollution not only can pass through the filtering component 2 of the movable filtering device B1 but also can be guided by the directional blower 1a and discharged out of the indoor space by the ventilator B2 when the filtering device B is driven to generate a directed air convection by receiving the control command. It should be noted that the implementation mentioned above is only for an embodiment but the present invention is not limited thereto.

Please refer to FIG. 1. The gas detection devices A are disposed in the indoor space to detect the qualitative property and the concentration of the air pollution, and each of the gas detection devices A detects the air pollution to output an air pollution data for performing an intelligent computation.

Furthermore, it is understood that, as shown in FIG. 2B and FIG. 2D, the filtering component 2 of the physical type filtering device B is a filter to block and absorb the air pollution so as to filter the air pollution physically. In some embodiments, the filter is a high-efficiency particulate air filter 2a for absorbing the chemical smog, bacteria, dusts, particles, and pollens contained in the polluted air, thereby the filtration and purification are made by introducing the polluted air into the system. The filtering component 2 of the chemical type filtering device B filters the air pollution chemically by coating a degradation layer 21 on the filtering component 2. In some embodiments, the degradation layer 21 may be an activated carbon 21a for filtering organic substances, inorganic substances, colored substances, and/or odor substances. In some embodiments, the degradation layer 21 may be a cleansing factor layer 21b with chlorine dioxide for inhibiting the activity of viruses, bacteria, fungus, influenza A virus, influenza B virus, Enterovirus, and Norovirus in the polluted air introduced into the system, accordingly, the suppressing rate may exceed 99%, allowing the reduction of the cross infections of the viruses. In some embodiments, the degradation layer 21 may be an herbal protection coating layer 21c including the extracts of *Rhus chinensis* Mill (may be *Rhus chinensis* Mill from Japan) and the extracts of *Ginkgo biloba* to efficiently perform anti-allergy function for degrading cell surface proteins of influenza viruses (e.g., influenza virus subtype H1N1). In some embodiments, the degradation layer 21 may be a layer of silver ions 21d for suppressing the activity of surface protein on the viruses, bacteria, and fungus in the polluted air introduced into the system. In some embodiments, the degradation layer 21 may be a zeolite mesh 21e for removing ammonia, heavy metals, organic pollutants, *Escherichia coli*, phenol, chloroform, or anion surfactants. In some embodiments, the filtering component 2 of the chemical type filtering device B filters the air pollution chemically along with a light illumination 22, wherein the light illumination 22 is a photocatalyst unit including a photocatalyst 22a and an ultraviolet light 22b, when the photocatalyst 22a is illuminated by the ultraviolet light 22b, the light energy is converted into electrical energy to degrade the hazardous matters in the polluted air to achieve the effect of filtration and purification. In some embodiments, the light illumination 22 is a photo plasma unit including a nanometer light tube 22c, wherein the introduced polluted air is illuminated by the nanometer light tube 22c, making the oxygen molecules and water molecules in the polluted air decompose into photo plasma with high oxidative power for generating a plasma flow which is capable to make the degradation of the organic molecules, accordingly, the volatile organic compounds (VOC) such as formaldehyde and toluene in the polluted air can be decomposed into water and carbon dioxide. In some embodiments, the filtering component 2 of the chemical type filtering device B filters the air pollution chemically along with a degradation unit 23. In some embodiments, the degradation unit 23 is a negative ion unit 23a, thus the particulates carry with positive charges in the polluted air are adhered to the negative charges on the negative ion unit 23a through applying high voltage discharging to the introduced polluted air. In some embodiments, the degradation unit 23 is a plasma ion unit 23b, when the polluted air is introduced into the system, the oxygen molecules and the water molecules in the polluted air are ionized to generate cations ($H^+$) and anions ($O_2^-$), Therefore, the substances with water molecules around the ions attach on the surfaces of viruses and bacteria will convert the water molecules into oxidative oxygen ions (hydroxyl ions, $OH^-$ ions) with high oxidative power under chemical reaction, the oxidative oxygen ions will take away the hydrogen ions of the proteins on the surfaces of the viruses and the bacteria to make oxidation and decomposition reaction for the filtration of the introduced air.

As shown in FIG. 2A, according to one or some embodiments of the present invention, each of the filtering devices B includes at least one blower 1 and at least one filtering component 2. The blower 1 has the ability of transmitting the air bi-directionally, including the extraction and ejection. In some embodiment, the arrow shown in the figures indicates the direction of the gas (air) flow. The blower 1 may be disposed in front of the filtering component 2, or behind the filtering component 2, in another embodiment, the blowers 1 may be disposed in front of and behind the filtering component 2 simultaneously; namely the blower 1 can be adjusted according to actual application.

It is noted that, the control central processor C receives the indoor air pollution data detected by the indoor gas detection devices A to perform the intelligent computation.

The intelligent computation performs artificial intelligent (AI) computation and big data comparison to locate the air pollution location in the indoor space. Furthermore, the control central processor C transmits the control command intelligently and selectively to the filtering devices B through wireless communication to drive the filtering devices B, achieving the rapid filtration of air pollution by the at least one filtering component 2.

It is noted that, the transmission is performed by a wireless communication, and the wireless communication is implemented by using a Wi-Fi module, a Bluetooth module, a radiofrequency identification (RFID) module, or a near field communication module.

In one embodiment, as shown in FIG. 3A or FIG. 3C, the filtering device B includes at least one physical or chemical type movable filtering device B1. The structure of the physical or chemical type movable filtering device B1 is the same as the structure of the physical or chemical type filtering device B, and the physical or chemical type movable filtering device B1 represents a filtering device B which is autonomous movable. In another embodiment, as shown in FIG. 3C, the filtering device B includes at least one movable filtering device B1, wherein the movable filtering device B1 further comprises a directional blower 1a capable of generating an air convection, the directional blower 1a can be moved upward and downward, as well as being rotated with respect to the movable filtering device B1 to perform the air convection within a certain direction.

It is noted that, in one embodiment, the control central processor C is configured to receive the outdoor air pollution data detected by the at least one outdoor gas detection device A0 and the indoor air pollution data detected by the indoor gas detection devices A to perform the intelligent computation. The intelligent computation figures out a highest data among the indoor air pollution data to determine the air pollution location in the indoor space, also, the control command is intelligently and selectively transmitted to a filtering device B at the air pollution location to enable the filtering device B, and the control command is intelligently and selectively transmitted to rest of the filtering devices B which are outside the air pollution location to enable the rest of the filtering devices B to generate the air convection directed to the air pollution. The air convection accelerates the filtering of the air pollution at the air pollution location and the air pollution outside the air pollution location which is diffused, moved, and directed by the air convection, and the filtering components 2 of the rest of the filtering devices B outside the air pollution location are enabled intelligently and selectively, therefore the air pollution in the indoor space is filtered to allow the indoor air pollution data of the indoor space to be lowered to the safety detection value in which the air pollution data approaches to almost zero (the non-detection state), and the gas in the indoor space is cleaned to the safe and breathable state.

It is noted that, in another embodiment, the control central processor C is configured to receive the outdoor air pollution data detected by the at least one outdoor gas detection device A0 and the indoor air pollution data detected by the indoor gas detection devices A to perform the intelligent computation. After the intelligent computation makes the comparison of the indoor air pollution data of the indoor space detected by at least three of the indoor gas detection devices A, the indoor air pollution location in the indoor space is determined according to the indoor air pollution data detected by the at least three of the indoor gas detection devices A through the intelligent computation, the control command is intelligently and selectively transmitted to a filtering device B nearby the air pollution location to enable the filtering device B and transmitted to a movable filtering device B1 to enable the movable filtering device B1 to move toward the air pollution location, thus accelerating the air pollution to be filtered by the filtering components 2 of the filtering device B and the movable filtering device B1 at the air pollution location, and the control command is intelligently and selectively transmitted to rest of the filtering devices B which are outside the air pollution location to enable the rest of the filtering devices B for generating the air convection directed to the air pollution; the air convection accelerates the filtering of the air pollution at the air pollution location and the air pollution outside the air pollution location which is diffused, moved, and directed by the air convection, and the filtering components 2 of the rest of the filtering devices B outside the air pollution location are enabled intelligently and selectively, thus the air pollution in the indoor space is filtered to allow the indoor air pollution data of the indoor space to be lowered to the safety detection value in which the air pollution data approaches to almost zero (the non-detection state), and the air in the indoor space is cleaned to the safe and breathable state. In other words, in some embodiments, if the intelligent computation determines that the air pollution location is near the electric fan B4, the control command is wirelessly transmitted to enable the movable filtering device B1, thereby the movable filtering device B1 is moved nearby the electric fan B4 to clean the air pollution. The control command may be wirelessly transmitted to the electric fan B4. Under this configuration, the electric fan B4 can filter the air pollution through the filtering device B of the electric fan B4, the air flow can be delivered toward the ventilator B2, and the control command is further wirelessly transmitted to the ventilator B2 to enable the operation of the ventilator B2, so that the air pollution in the indoor space can be rapidly cleaned or discharged outside.

Moreover, it is noted that, the filtering device B includes a movable filtering device B1, and the movable filtering device B1 includes an indoor gas detection device A. The indoor gas detection device A is configured to receive the control command to move toward the air pollution location, and a directional blower 1a is capable of being moved upward and downward as well as being rotated with respect to the movable filtering device B1 to perform the air convection within a certain direction, thus accelerating the air pollution to be filtered by the filtering components 2 of the filtering device B and the movable filtering device B1 nearby the air pollution location. Moreover, during the movable filtering device B is moving toward the air pollution location, the directional blower 1a is enabled, and the control command is intelligently and selectively transmitted to rest of the filtering devices B which are outside the air pollution location to enable the rest of the filtering devices B to generate the air convection directed to the air pollution. The air convection accelerates the filtering of the air pollution at the air pollution location and the air pollution outside the air pollution location which is diffused, moved, and directed by the air convection, and the filtering components 2 of the rest of the filtering devices B outside the air pollution location are enabled intelligently and selectively, so that the air pollution in the indoor space is filtered to allow the indoor air pollution data of the indoor space to be lowered to the safety detection value in which the air pollution data approaches to the non-detection state, and the air in the indoor space is cleaned to the safe and breathable state. In brief, in some embodiments, if the air pollution location is nearby the electric fan B4, the control command is wirelessly transmitted to enable the movable filtering device B1, and the movable filtering device B1 with the directional blower 1a is moved to the air pollution location (nearby the electric fan B4), so that the directional blower 1a can provide an air convection with a certain direction, thereby accelerating the air pollution to be cleaned by the filtering device B nearby the air pollution location. For example, the air convection guides the air pollution to the filtering component of the electric fan B4 for cleaning, and the electric fan B4 further delivers the air flow toward the ventilator B2, so that the air pollution is discharged from the indoor space to the outdoor space through the ventilator B2. Under this configuration, the movable filtering device B1 can clean the air pollution, the electric fan B4 can filter the air pollution through the filtering device B of the electric fan B4, the air flow can be delivered toward the ventilator B2, so that the air pollution in the indoor space can be quickly cleaned or discharged outside.

In one embodiment, the indoor gas detection devices A output the indoor air pollution data after detecting the air pollution in the indoor space, then the indoor air pollution data of the indoor space is received and compared by the control central processor C to obtain a highest data through the intelligent computation, thus the air pollution location in the indoor space can be determined. In addition, the control command is intelligently and selectively transmitted to the filtering device B at the air pollution location and the movable filtering device B1 respectively to enable the filtering device B and the movable filtering device B1 to move toward the air pollution location, accelerating the air pollution to be filtered by the filtering components 2 of the filtering device B and the movable filtering device B1 at the air pollution location. Furthermore, the control command is intelligently and selectively transmitted to the rest of the filtering devices B which are outside the air pollution location, enabling the rest of the filtering devices B to generate the air convection directed to the air pollution. As a result, the air convection accelerates the filtering of the air pollution at the air pollution location and the air pollution outside the air pollution location which is diffused, moved, and directed by the air convection; on the other hand, the filtering components 2 of the rest of the filtering devices B outside the air pollution location are enabled intelligently and selectively, thereby the air pollution in the indoor space is filtered to allow the indoor air pollution data of the indoor space to be lowered to the safety detection value, in which the air pollution data approaches to the non-detection state, and the air in the indoor space is cleaned to the safe and breathable state. In other words, according to one or some embodiments of the present invention, the air pollution location can be located from the highest data among the indoor air pollution data, and the system intelligently and selectively transmits the control command to the filtering device B nearby the air pollution location and the movable filtering device B1 respectively, enabling the filtering device B and the movable filtering device B1 to move toward the air pollution location, also, the control command is transmitted to the rest of the filtering devices B which are outside the air pollution location to enable the rest of the filtering devices B. Therefore, the air pollution can be filtered by the filtering components 2 of the filtering devices B and the movable filtering device B1. Hence, not only the air pollution can be filtered by the filtering device B nearby the air pollution location, but also the movable filtering device B1 can move toward the air pollution location to accelerate the filtering through the filtering component 2 of the movable filtering device B1. Moreover, during the filtering process, the system further intelligently and selectively enables rest of the filtering devices B which are outside the air pollution location to filter the air pollution which is diffusing and moving, thereby accelerating the filtering of the air pollution in the indoor space to allow the air pollution in the indoor space to be lowered to the safety detection value, and the 18 as air in the indoor space is cleaned to a safe and breathable state. In other words, in some embodiments, the air pollution can be filtered to allow the indoor air pollution data of the indoor space to be lowered to the safety detection value, and the air pollution can be filtered rapidly, allowing the indoor air pollution data to approach to the non-detection state. The safety detection value includes that the indoor air pollution data is approaching to almost zero (the non-detection state), therefore the air pollution is cleaned to the safe and breathable state, and the performance of locating, guiding, cleaning, and filtering the air pollution can be achieved.

In another embodiment, the indoor gas detection devices A output the indoor air pollution data after detecting the air pollution, the indoor air pollution data of the indoor space is received and compared by the control central processor C, wherein the indoor air pollution data is detected by at least three of the indoor gas detection devices A, the air pollution location in the indoor space is determined according to the indoor air pollution data detected by the at least three of the indoor gas detection devices A through the intelligent computation, then the control command is intelligently and selectively transmitted to a filtering device B at the air pollution location and the movable filtering device B1 respectively, enabling the filtering device B and the movable filtering device B1 to move toward the air pollution location, accelerating the air pollution to be filtered by the filtering components 2 of the filtering device B and the movable filtering device B at the air pollution location. In addition, the control command is intelligently and selectively transmitted to rest of the filtering devices B which are outside the air pollution location to enable the rest of the filtering devices B to generate the air convection directed to the air pollution. As a result, the air convection accelerates the filtering of the air pollution at the air pollution location and the air pollution outside the air pollution location which is diffused, moved, and directed by the air convection, also, the filtering components 2 of the rest of the filtering devices B outside the air pollution location are enabled intelligently and selectively, so that the air pollution in the indoor space is filtered, allowing the indoor air pollution data of the indoor space to be lowered to the safety detection value, in which the air pollution data approach to the non-detection state, and the air in the indoor space is cleaned to the safe and breathable state.

In other words, in this embodiment, the air pollution location can be located from at least three data through the intelligent computation, the system intelligently and selectively transmits the control command to the filtering device B nearby the air pollution location and the movable filtering device B1 respectively, enabling the filtering device B and the movable filtering device B1 to move toward the air pollution location, furthermore, the control command is also transmitted to rest of the filtering devices B outside the air pollution location to enable the rest of the filtering devices B, therefore, the air pollution can be filtered by the filtering components 2 of the filtering devices B and the movable filtering device B1. Hence, not only the air pollution can be filtered by the filtering device B nearby the air pollution location, but also the movable filtering device B1 can move toward the air pollution location to accelerate the filtering through the filtering component 2 of the movable filtering device B1. Moreover, during the filtering process, the system further enables rest of the filtering devices B which are outside the air pollution location intelligently and selectively to filter the air pollution which is diffusing and moving, thereby accelerating the filtering of the air pollution to allow the air pollution in the indoor space to be lowered to the safety detection value, and the air in the indoor space is cleaned to a safe and breathable state. In other words, in some embodiments, the air pollution can be filtered to allow the indoor air pollution data of the indoor space to be lowered to the safety detection value, and the air pollution can be filtered rapidly to allow the indoor air pollution data to approach to the non-detection state. The safety detection value includes that the indoor air pollution data is approaching to the non-detection state, thus the air pollution is cleaned to the safe and breathable state, and the performance of locating, guiding, cleaning, and filtering the air pollution can be achieved.

In one embodiment, the indoor gas detection devices A output the indoor air pollution data after detecting the air pollution, the indoor air pollution data of the indoor space is received and compared by the control central processor C to obtain a highest data among the indoor air pollution data through the intelligent computation for determining the air pollution location in the indoor space, then the control command is intelligently and selectively transmitted to a filtering device B at the air pollution location and the movable filtering device B1 respectively, enabling the filtering device B and the movable filtering device B1 to move toward the air pollution location. Moreover, during the movable filtering device B1 is moving to the air pollution location, the directional blower 1*a* is enabled, accelerating the air pollution to be filtered by the filtering components 2 of the filtering device B and the movable filtering device B1 at the air pollution location. Moreover, the control command is intelligently and selectively transmitted to rest of the filtering devices B which are outside the air pollution location to enable the rest of the filtering devices B and generate the air convection directed to the air pollution, wherein the air convection accelerates the filtering of the air pollution at the air pollution location and the air pollution outside the air pollution location which is diffused, moved, and directed by the air convection. Furthermore, the filtering components 2 of the rest of the filtering devices B outside the air pollution location are enabled intelligently and selectively, thereby the air pollution in the indoor space is filtered to allow the indoor air pollution data of the indoor space to be lowered to the safety detection value in which the air pollution data approaches to the non-detection state, allowing the air in the indoor space to be cleaned to the safe and breathable state. In other words, in this embodiment, the air pollution location can be located from the air pollution data, and the system intelligently and selectively transmits the control command to the filtering device B nearby the air pollution location to enable the filtering device B. Further, the system intelligently and selectively transmits the control command to the movable filtering device B1 to enable the movable filtering device B1 to move toward the air pollution location, enables the directional blower 1*a* during the movable filtering device B1 is moved to the air pollution location, the system also intelligently and selectively transmits the control command to rest of the filtering devices B which are outside the air pollution location to enable the rest of the filtering devices B. Therefore, the air pollution can be filtered by the filtering components 2 of the filtering devices B and the movable filtering device B1. Hence, not only the air pollution can be filtered by the filtering device B nearby the air pollution location and the movable filtering device B1 can move toward the air pollution location, but also the directional blower 1a is enabled to accelerate the filtering through the filtering component 2 of the movable filtering device B1. Moreover, during the filtering process, the system further enables rest of the filtering devices B outside the air pollution location intelligently and selectively to filter the air pollution which is diffusing and moving, thereby accelerating the filtering of the air pollution to allow the indoor air pollution data to be lowered to the safety detection value, and the gas in the indoor space is cleaned to a safe and breathable state. In other words, in some embodiments, the air pollution can be filtered to allow the indoor air pollution data to be lowered to the safety detection value, and the air pollution can be filtered rapidly to allow the indoor air pollution data to approach to the non-detection state. The safety detection value includes that the indoor air pollution data is approaching to the non-detection state, therefore the air pollution is cleaned to the safe and breathable state, and the performance of locating, guiding, cleaning, and filtering the air pollution can be achieved.

It should be understood in the present invention, the system provides the control central processor C to receive the outdoor air pollution data detected by the at least one outdoor gas detection device A0 and the indoor air pollution data detected by the indoor gas detection devices A, then the air pollution data is transmitted to a cloud processing device E. The cloud processing device E locates the air pollution location in the indoor space through the artificial intelligent computation and big data comparison, and the cloud processing device E intelligently and selectively transmits the control command to the control central processor C. As shown in FIG. 1, the indoor gas detection devices A can be freely disposed at any position within the indoor space, and each of the filtering devices B includes an indoor gas detection device A which is utilized along with the blower 1 of the filtering device B, thus the qualitative property and the concentration of the air pollution at the location of the filtering device B can be detected, as well as the air pollution data can be outputted to perform the intelligent computation. Therefore, after the control central processor C receives the indoor air pollution data of the indoor space detected by the indoor gas detection devices A (including the indoor gas detection device A in the filtering device B), the indoor air pollution data is transmitted to the cloud processing device E to perform the intelligent computation. Hence, through artificial intelligent (AI) computation and big data comparison, the air pollution location in the indoor space can be located, and cloud processing device E transmits the control command to the control central processor C, so that the control central processor C controls the filtering devices B to enable the filtering devices B.

To illustrate the embodiments of the present invention clearly, the detail structures of the outdoor gas detection device A0 and the indoor gas detection device A are illustrated as below.

Please refer to FIG. 4A to FIG. 11. In some embodiments of the present invention each of the outdoor gas detection device A0 and the indoor gas detection device A is a gas detection device 3. The gas detection device 3 includes a control circuit board 31, a gas detection main body 32, a microprocessor 33, and a communication device 34. The gas detection main body 32, the microprocessor 33, and the communication device 34 are integrally packaged with the control circuit board 31 and electrically connected to each other. The microprocessor 33 and the communication device 34 are disposed on the control circuit board 31, and the microprocessor 33 controls a driving signal of the gas detection main body 32 to enable the operation of the gas detection main body 32, so that the gas detection main body 32 detects the air pollution and outputs a detection signal, furthermore, the microprocessor 33 receives the detection signal to compute, process, and output the air pollution data, providing the communication device 34 with the air pollution data for wirelessly transmitting outwardly to the control central processor C.

Please refer to FIG. 4A to FIG. 9A. In one or some embodiments, the gas detection main body 32 includes a base 321, a piezoelectric actuator 322, a driving circuit board 323, a laser component 324, a particulate sensor 325, and an outer cover 326. The base 321 comprises a first surface 3211, a second surface 3212, a laser installation region 3213, a gas inlet groove 3214, a gas-guiding component installation region 3215, and a gas outlet groove 3216. The first surface 3211 and the second surface 3212 are opposite to each other. The laser installation region 3213 is formed by hollowing out the base 321 from the first surface 3211 to the second surface 3212 for accommodating the laser component 324. The outer cover 326 covers the base 321 and has a side plate 3261. The side plate 3261 has a gas inlet opening 3261a and a gas outlet opening 3261b. The gas inlet groove 3214 is recessed from the second surface 3212 and located adjacent to the laser installation region 3213. The gas inlet groove 3214 has a gas inlet through hole 3214a and two lateral walls. The gas inlet through hole 3214a is in communication with the outside environment of the base 321 and is corresponding to the gas inlet opening 3261a of the outer cover 326. Two light penetration windows 3214b penetrate the two lateral walls of the gas inlet groove 3214 and are in communication with the laser installation region 3213. Therefore, when the first surface 3211 of the base 321 is covered by the outer cover 326, and the second surface 3212 of the base 321 is covered by the driving circuit board 323, a gas inlet path can be defined by the gas inlet groove 3214.

The gas-guiding component installation region 3215 is recessed from the second surface 3212 and in communication with the gas inlet groove 3214. A ventilation hole 3215a penetrates a bottom surface of the gas-guiding component installation region 3215. Each of the four corners of the gas-guiding component installation region 3215 has a positioning bump 3215b. The gas outlet groove 3216 has a gas outlet through hole 3216a, and the gas outlet through hole 3216a is corresponding to the gas outlet opening 3261b of the outer cover 326. The gas outlet groove 3216 includes a first region 3216b and a second region 3216c. The first region 3216b is recessed from a portion of the first surface 3211 corresponding to a vertical projection region of the gas-guiding component installation region 3215. The second region 3216c is at a portion extending from a region that is not corresponding to the vertical projection region of the gas-guiding component installation region 3215, and the second region 3216c is hollowed out from the first surface 3211 to the second surface 3212. The first region 3216b is connected to the second region 3216c to form a stepped structure. Moreover, the first region 3216b of the gas outlet groove 3216 is in communication with the ventilation hole 3215a of the gas-guiding component installation region 3215, and the second region 3216c of the gas outlet groove 3216 is in communication with the gas outlet through hole 3216a. Therefore, when the first surface 3211 of the base 321 is covered by the outer cover 326 and the second surface 3212 of the base 321 is covered by the driving circuit board 323, a gas outlet path can be defined by the gas outlet groove 3216 and the driving circuit board 323.

Furthermore, the laser component 324 and the particulate sensor 325 are disposed on the driving circuit board 323 and located in the base 321. The laser component 324 and the particulate sensor 325 are electrically connected to the driving circuit board 323. It should notice that the driving circuit board 323 is omitted to clearly explain the positions of the laser component 324, the particulate sensor 325, and the base 321. In the embodiment of the present invention, the laser component 324 is located at the laser installation region 3213 of the base 321. The particulate sensor 325 is located at the gas inlet groove 3214 of the base 321 and aligned with the laser component 324. Moreover, the laser component 324 is corresponding to the light penetration windows 3214b so as to allow the light beam emitted by the laser component 324 to pass therethrough and into the gas inlet groove 3214. The light path of the light beam emitted by the laser component 324 passes through the light penetration windows 3214b and is orthogonal to the gas inlet groove 3214. The light beam emitted by the laser component 324 passes into the gas inlet groove 3214 through the light penetration windows 3214b, thereby the particulate matters in the gas inlet groove 3214 is illuminated by the light beam. When the light beam contacts the gas, the light beam will be scattered and generate light spots. Hence, the light spots generated by the scattering are received and calculated by the particulate sensor 325 located at the position orthogonal to the gas inlet groove 3214 to obtain the detection data of the gas. Furthermore, a gas sensor 327 is disposed on the driving circuit board 323 and is located at the gas outlet groove 3216 for detecting the polluted gas introduced into the gas outlet groove 3216, and the gas sensor 327 is electrically connected to the driving circuit board 323. In one embodiment of the present invention, the gas sensor 327 includes at least one selected from the group consisting of a volatile organic compound detector capable of detecting gas information of carbon dioxide ($CO_2$) or total volatile organic compounds (TVOC), a formaldehyde sensor capable of detecting gas information of formaldehyde (HCHO) gas, a bacterial sensor capable of detecting information of bacteria or fungi, and a virus sensor capable of detecting information of viruses, and any combination thereof.

Moreover, the piezoelectric actuator 322 is located at the square-shaped gas-guiding component installation region 3215 of the base 321, and the gas-guiding component installation region 3215 is in communication with the gas inlet groove 3214. When the piezoelectric actuator 322 is enabled, the gas in the gas inlet groove 3214 is inhaled into the piezoelectric actuator 322, passing through the ventilation hole 3215a of the gas-guiding component installation region 3215, and entering the gas outlet groove 3216. Moreover, the driving circuit board 323 covers the second surface 3212 of the base 321. The laser component 324 and the particulate sensor 325 are disposed on the driving circuit board 323 and electrically connected to the driving circuit board 323. As the outer cover 326 covers the base 321, the gas inlet opening 3261a is corresponding to the gas inlet through hole 3214a of the base 321, and the gas outlet opening 3216b is corresponding to the gas outlet through hole 3216a of the base 321.

Furthermore, the piezoelectric actuator 322 includes a nozzle plate 3221, a chamber frame 3222, an actuation body 3223, an insulation frame 3224, and a conductive frame 3225. The nozzle plate 3221 is made by a flexible material and has a suspension sheet 3221a and a hollow hole 3221b. The suspension sheet 3221a is a flexible sheet which can bend and vibrate. The shape and the size of the suspension sheet 3221a approximately corresponding to the inner edge of the gas-guiding component installation region 3215. The hollow hole 3221b penetrates through the center portion of the suspension sheet 3221a for the gas flowing therethrough. In one embodiment of the present invention, the shape of the suspension sheet 3221a can be selected from square, circle, ellipse, triangle, or polygon.

Furthermore, the chamber frame 3222 is stacked on the nozzle plate 3221, and the shape of the chamber frame 3222 is corresponding to the shape of the nozzle plate 3221. The actuation body 3223 is stacked on the chamber frame 3222. A resonance chamber 3226 is collectively defined between the actuation body 3223, the chamber frame 3222, and the suspension sheet 3221a. The insulation frame 3224 is stacked on the actuation body 3223. The appearance of the insulation frame 3224 is similar to the appearance of the chamber frame 3222. The conductive frame 3225 is stacked on the insulation frame 3224. The appearance of the conductive frame 3225 is similar to the appearance of the insulation frame 3224. The conductive frame 3225 has a conductive pin 3225a and a conductive electrode 3225b. The conductive pin 3225a extends outwardly from the outer edge of the conductive frame 3225, and the conductive electrode 3225b extends inwardly from the inner edge of the conductive frame 3225. Moreover, the actuation body 3223 further includes a piezoelectric carrying plate 3223a, an adjusting resonance plate 3223b, and a piezoelectric plate 3223c. The piezoelectric carrying plate 3223a is stacked on the chamber frame 3222, and the adjusting resonance plate 3223b is stacked on the piezoelectric carrying plate 3223a. The piezoelectric plate 3223c is stacked on the adjusting resonance plate 3223b. The adjusting resonance plate 3223b and the piezoelectric plate 3223c are accommodated in the insulation frame 3224. The conductive electrode 3225b of the conductive frame 3225 is electrically connected to the piezoelectric plate 3223c. In one preferred embodiment of the present invention, the piezoelectric carrying plate 3223a and the adjusting resonance plate 3223b are both made of conductive material(s). The piezoelectric carrying plate 3223a has a piezoelectric pin 3223d. The piezoelectric pin 3223d and the conductive pin 3225a are in electrical connection with a driving circuit (not shown) of the driving circuit board 323 to receive a driving signal (which may be a driving frequency and a driving voltage). The piezoelectric pin 3223d, the piezoelectric carrying plate 3223a, the adjusting resonance plate 3223b, the piezoelectric plate 3223c, the conductive electrode 3225b, the conductive frame 3225, and the conductive pin 3225a may together generate an electrical circuit for transmitting the driving signal, and the insulation frame 3224 is provided for electrically insulating the conductive frame 3225 from the actuation body 3223 to avoid short circuit, thereby the driving signal can be transmitted to the piezoelectric plate 3223c. When the piezoelectric plate 3223c receives the driving signal, the piezoelectric plate 3223c deforms owing to the piezoelectric effect, and thus the piezoelectric carrying plate 3223a and the adjusting resonance plate 3223b are driven to vibrate in a reciprocating manner.

Moreover, the adjusting resonance plate 3223b is disposed between the piezoelectric plate 3223c and the piezoelectric carrying plate 3223a as a cushion element so as to adjust the vibration frequency of the piezoelectric carrying plate 3223a. Generally, the thickness of the adjusting resonance plate 3223b is greater than the thickness of the piezoelectric carrying plate 3223a. The thickness of the adjusting resonance plate 3223b may be modified to adjust the vibration frequency of the actuation body 3223.

Please refer to FIG. 7A, FIG. 7B, FIG. 8A, FIG. 8B, and FIG. 9A. The nozzle plate 3221, the chamber frame 3222, the actuation body 3223, the insulation frame 3224, and the conductive frame 3225 are sequentially stacked and assembled and are positioned in the gas-guiding component installation region 3215, thereby a clearance 3221c is defined between the suspension sheet 3221a and the inner edge of the gas-guiding component installation region 3215 for the gas to pass therethrough. A gas flow chamber 3227 is formed between the nozzle plate 3221 and the bottom surface of the gas-guiding component installation region 3215. The gas flow chamber 3227 is in communication with the resonance chamber 3226 formed between the actuation body 3223, the chamber frame 3222, and the suspension sheet 3221a through the hollow hole 3221b of the nozzle plate 3221. In one aspect of the present invention, the resonance chamber 3226 and the suspension sheet 3221a can generate the Helmholtz resonance effect to improve the transmission efficiency of the gas through controlling the vibration frequency of the gas in the resonance chamber 3226 to be close to the vibration frequency of the suspension sheet 3221a. When the piezoelectric plate 3223c moves in a direction away from the bottom surface of the gas-guiding component installation region 3215, the piezoelectric plate 3223c drives the suspension sheet 3221a of the nozzle plate 3221 to move in the direction away from the bottom surface of the gas-guiding component installation region 3215 correspondingly. Hence, the volume of the gas flow chamber 3227 expands dramatically, therefore the internal pressure of the gas flow chamber 3227 decreases and creates a negative pressure, drawing the gas outside the piezoelectric actuator 322 to flow into the piezoelectric actuator 322 through clearance 3221c and enter the resonance chamber 3226 through the hollow hole 3221b, thereby increasing the gas pressure of the resonance chamber 3226 and thus generating a pressure gradient. When the piezoelectric plate 3223c drives the suspension sheet 3221a of the nozzle plate 3221 to move toward the bottom surface of the gas-guiding component installation region 3215, the gas inside the resonance chamber 3226 is pushed to flow out quickly through the hollow hole 3221b to further push the gas inside the gas flow chamber 3227, thereby the converged gas can be quickly and massively ejected out of the gas flow chamber 3227 through the ventilation hole 3215a of the gas-guiding component installation region 3215 in a state closing to an ideal gas state under the Bernoulli's law.

Figure 9A:
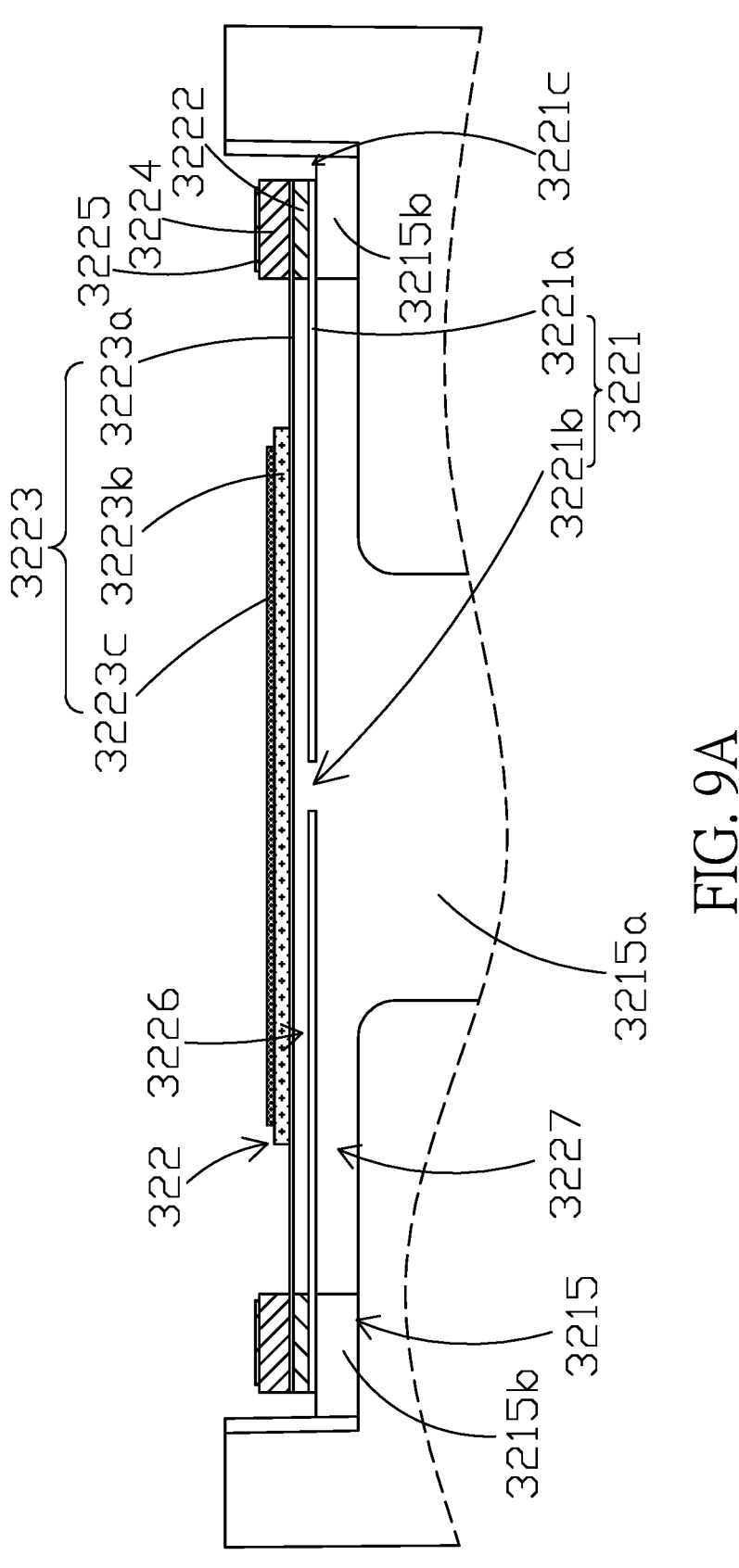
FIG. 9A illustrates a cross-sectional view (1) showing the operation of the piezoelectric actuator of the gas detection device in the present invention.
Figure 9B:
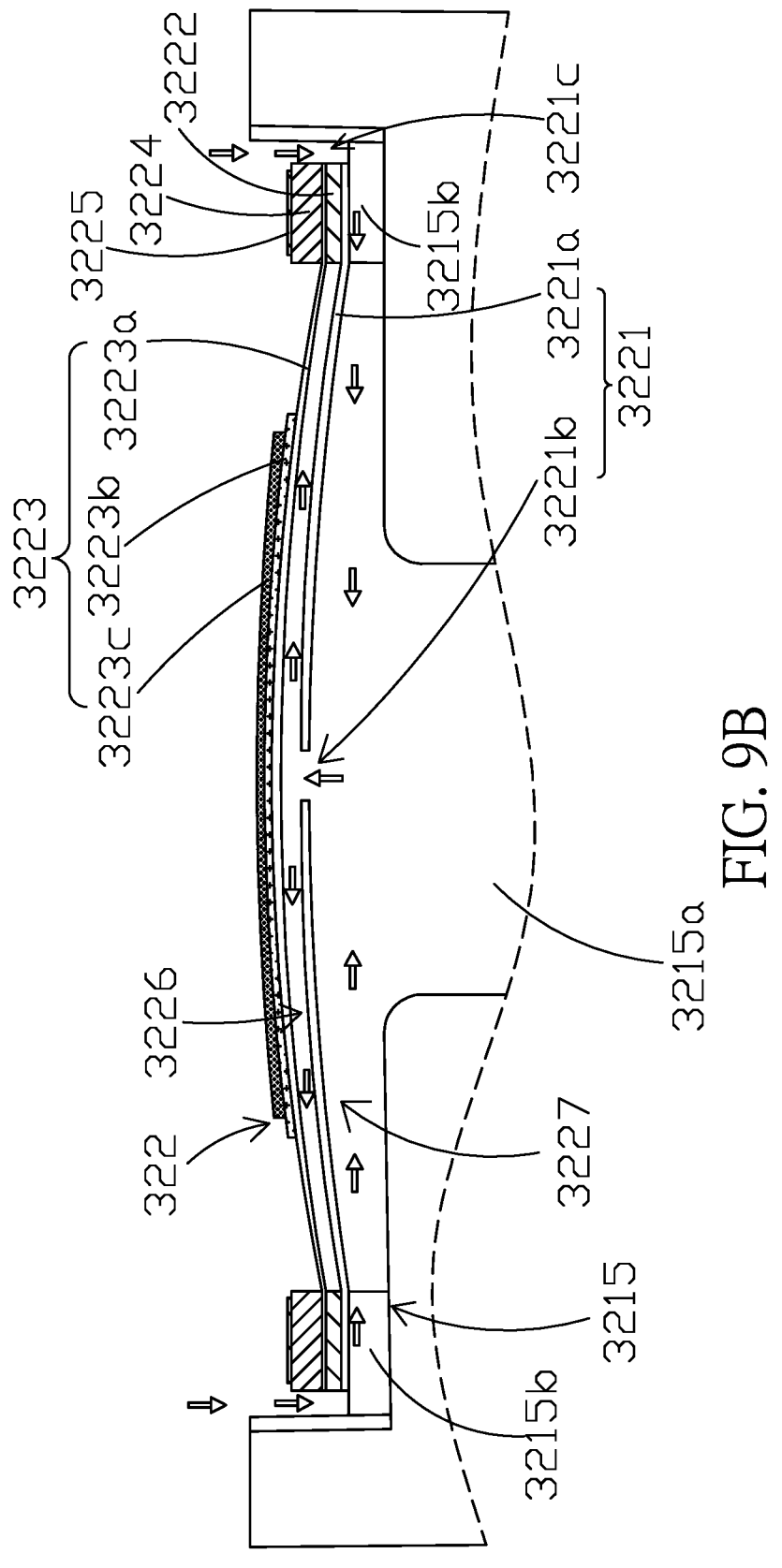
FIG. 9B illustrates a cross-sectional view (2) showing the operation of the piezoelectric actuator of the gas detection device in the present invention.
Figure 9C:
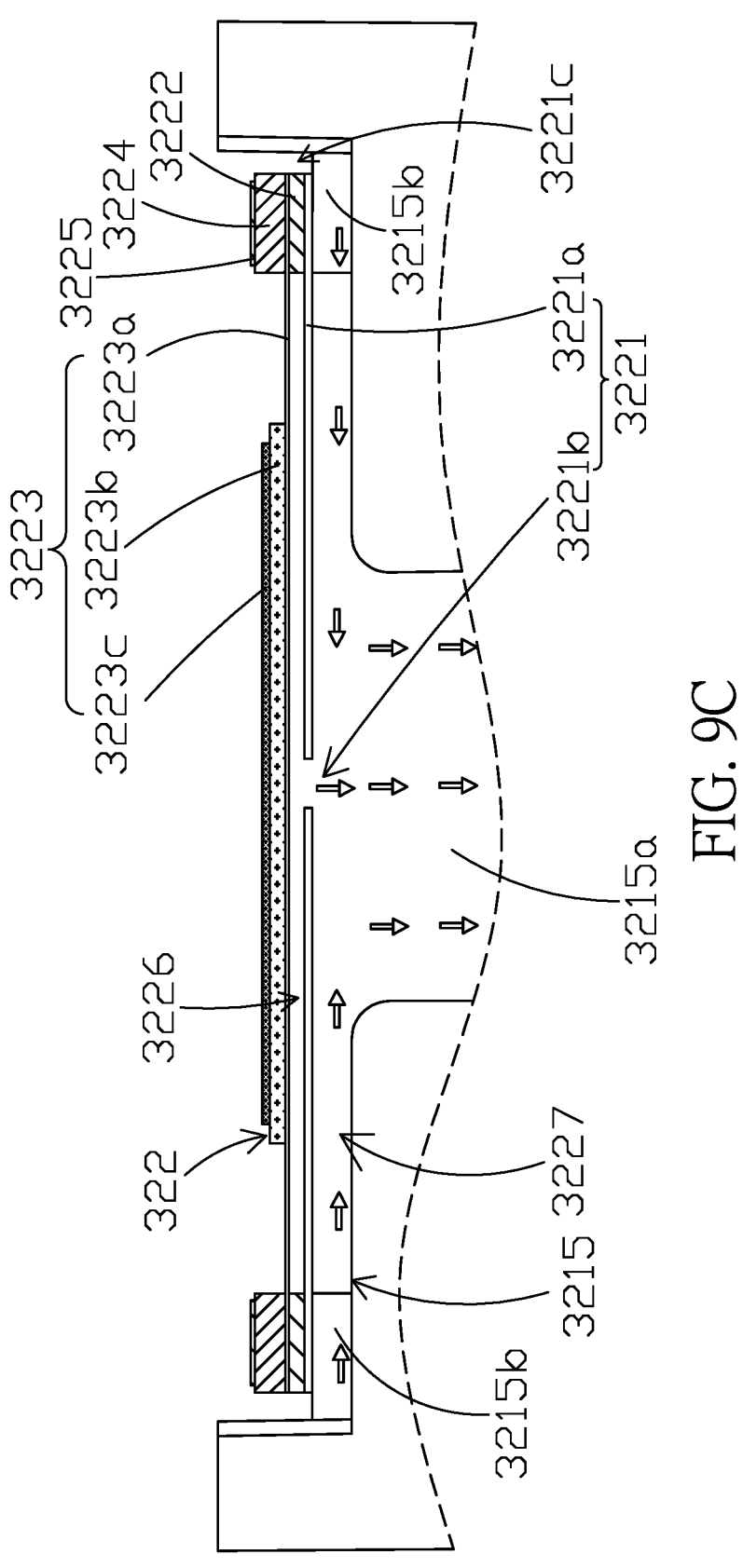
FIG. 9C illustrates a cross-sectional view showing the operation (3) of the piezoelectric actuator of the gas detection device in the present invention.
Figure 10A:
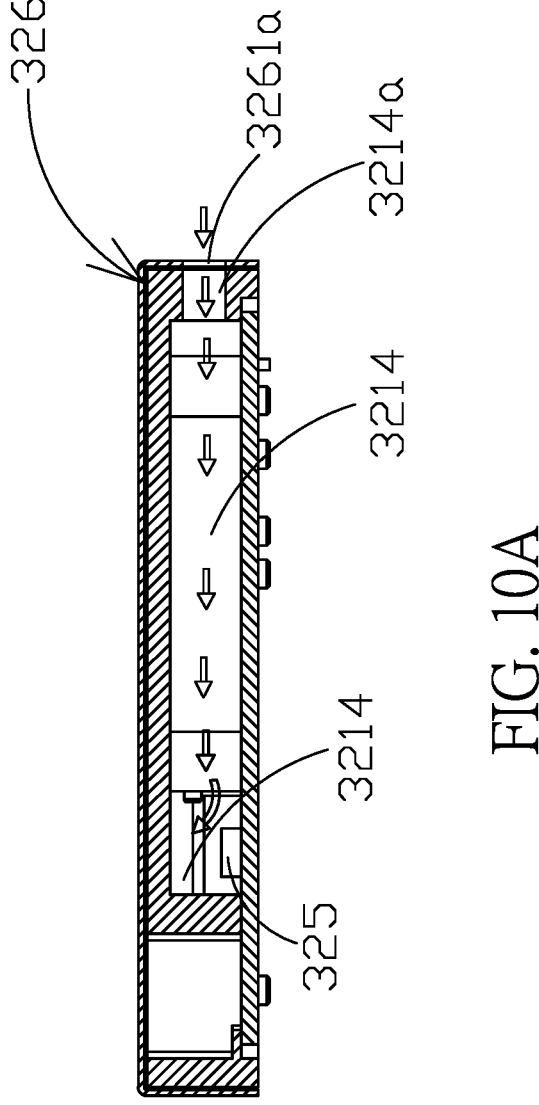
FIG. 10A illustrates a schematic cross-sectional view (1) of the gas detection main body of the gas detection device in the present invention.
Figure 10B:
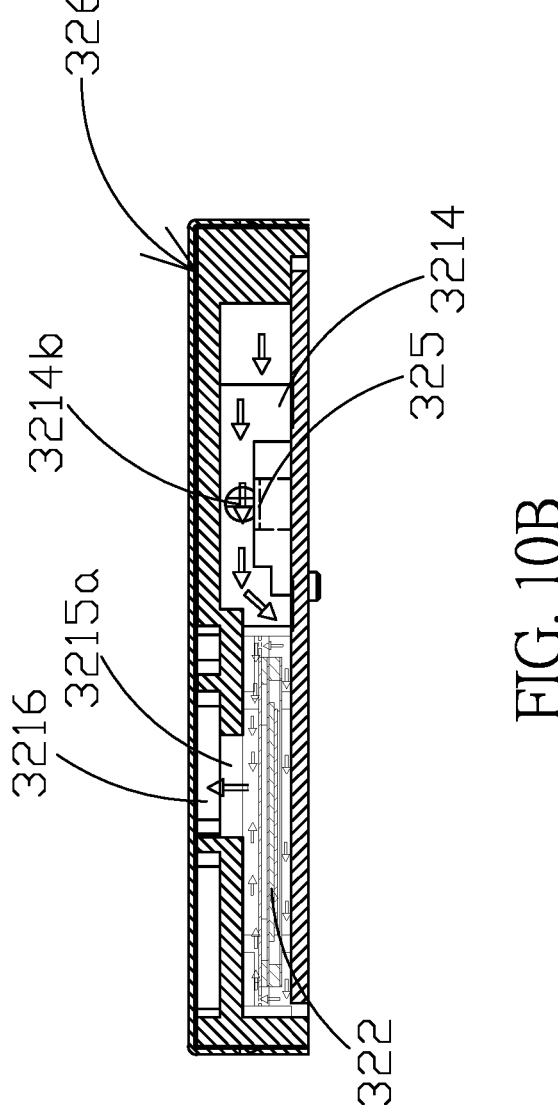
FIG. 10B illustrates a schematic cross-sectional view (2) of the gas detection main body of the gas detection device in the present invention.
Figure 10C:
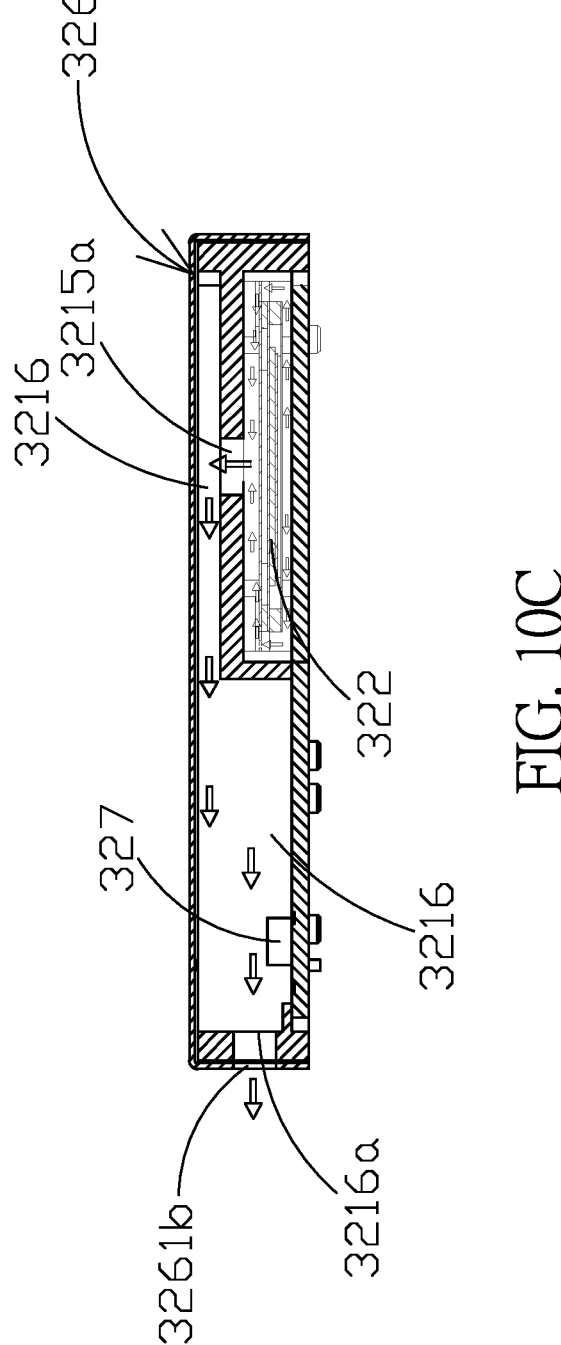
FIG. 10C illustrates a schematic cross-sectional view (3) of the gas detection main body of the gas detection device in the present invention.
Figure 11:
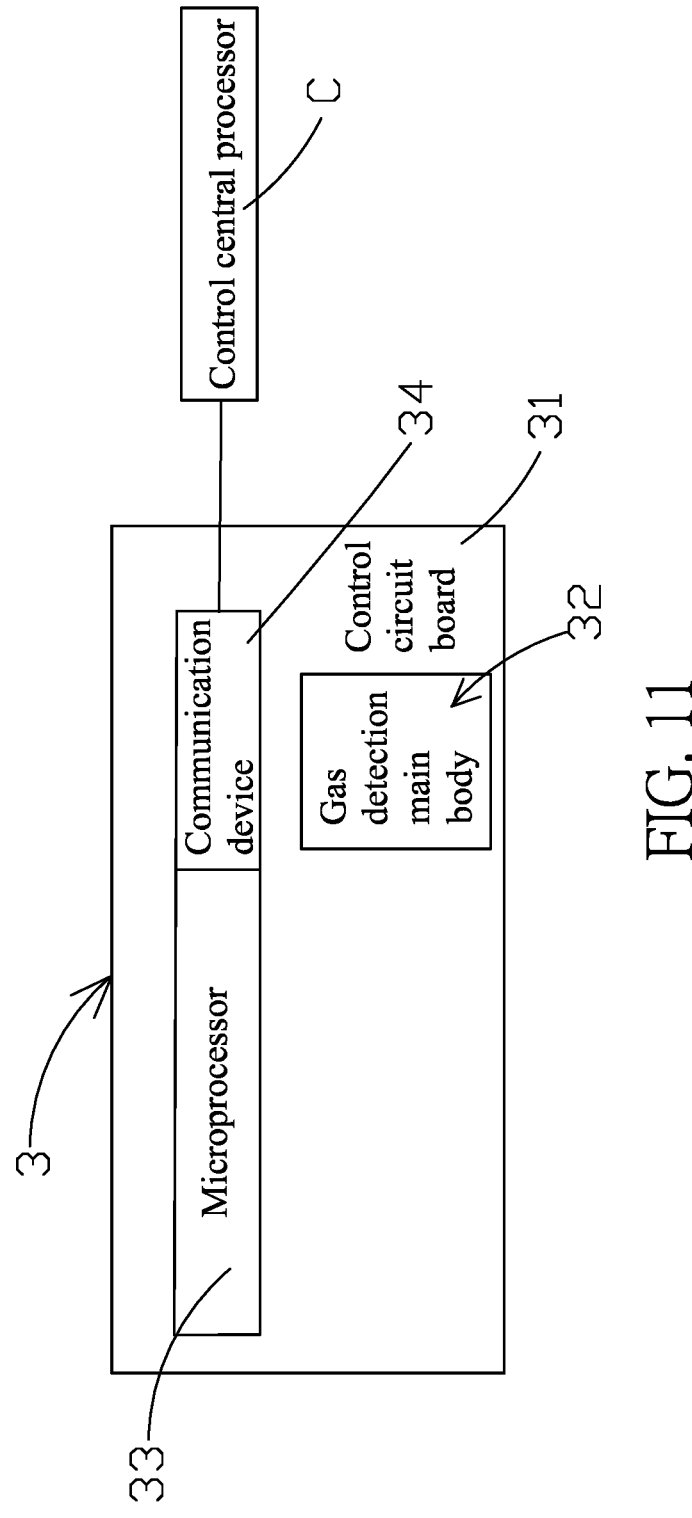
FIG. 11 illustrates a schematic view showing the transmission of the gas detection device in the present invention.

Therefore, through repeating the steps as shown in FIG. 9B and FIG. 9C, the piezoelectric plate 3223c can bend and vibrate in a reciprocating manner. Further, after the gas is discharged out of the resonance chamber 3226, the internal pressure of the resonance chamber 3226 is lower than the equilibrium pressure due to the inertia, as a result, the pressure difference guides the gas outside the resonance chamber 3226 into the resonance chamber 3226 again. Therefore, through controlling the vibration frequency of the gas in the resonance chamber 3226 to be close to the vibration frequency of the piezoelectric plate 3223c, the resonance chamber 3226 and the piezoelectric plate 3223c can generate the Helmholtz resonance effect so as to achieve effective, high-speed, and large-volume gas transmission of the gas. Moreover, the gas enters the gas detection main body 32 from the gas inlet opening 3261a of the outer cover 326, flows into the gas inlet groove 3214 of the base 321 through the gas inlet through hole 3214a, and reaches the position of the particulate sensor 325. Furthermore, the piezoelectric actuator 322 continuously drives the gas into the gas inlet path so as to facilitate the gas inside the detection main body 32 to stably and quickly pass through the particulate sensor 325. Next, the light beam emitted by the laser component 324 passes through the light penetration windows 3214b, enters the gas inlet groove 3214, and illuminates the gas in the gas inlet groove 3214 which passes through the particulate sensor 325. When the light beam from the particulate sensor 325 illuminates on the particulate matters in the gas, the light beam will be scattered and generate light spots. The particulate sensor 325 receives and calculates the light spots generated by the scattering to obtain the information of the particulate matters in the gas such as the particle size and the number of the particulate matters. Moreover, the gas passing through the particulate sensor 325 is continuously introduced into the ventilation hole 3215a of the gas-guiding component installation region 3215 by the piezoelectric actuator 322 and enters the gas outlet groove 3216. Finally, after the gas enters the gas outlet groove 3216, since the piezoelectric actuator 322 continuously delivers the gas into gas outlet groove 3216, therefore the gas is continuously pushed and discharged out of the gas detection main body 32 through the gas outlet through hole 3216a and the gas outlet opening 3261b.

In some embodiments, the gas detection device 3 not only can detect the particulate matters in the gas, but also can obtain the qualitative property of the gas introduced into the gas detection device 3. For example, the gas may be form-aldehyde, ammonia, carbon monoxide, carbon dioxide, oxy-gen, ozone, or the like. Therefore, the gas detection device 3 further includes a gas sensor 327. The gas sensor 327 is disposed on the driving circuit board 323 and is located at the gas outlet groove 3216 for detecting the polluted gas introduced into the gas outlet groove 3216, and the gas sensor 327 is electrically connected to the driving circuit board 323. Therefore, the gas sensor 327 can obtain the concentration or the property of the volatile organic com-pounds contained in the gas from the gas outlet path.

Next, the structure of the movable filtering device B1 is illustrated as below.

Please refer to FIG. 3A and FIG. 3B. The movable filtering device B1 includes a main body 40, a filtering component 2, a blower 1, an indoor gas detection device A, a controller module 45, a driving movable module 46, and a location checking unit 47. It is should noticed that, the specific details of structures and the functions of the blower 1, the filtering component 2, and the indoor gas detection device A have been mentioned as foregoing, thus it will not be iterated herein and after. Moreover, the movable filtering device B1 may include a rechargeable battery 44 electrically connected to the blower 1, the indoor gas detection device A, the controller module 45, the driving movable module 46, and the location checking unit 47 for providing the operation power for these components. Alternatively, in some embodi-ments, the rechargeable battery may be connected to the external power supply for the need of charge.

The main body 40 has an inlet opening 41, an outlet opening 42, and a gas passage 43. The gas passage 43 is disposed between the inlet opening 41 and the outlet open-ing 42, and the filtering component 2 is disposed in the gas passage 43 to filter the air pollution guided into the gas passage 43. The blower 1 is disposed in the gas passage 43 and at a central portion of the filtering component 2 to guide the air pollution from the inlet opening 41 to the outlet opening 42 therethrough the filtering component 2 for filtration and purification of the air pollution.

The controller module 45 is disposed in the main body 40, wherein the controller module 45 is electrically connected to the blower 1 and the indoor gas detection device A to receive the indoor air pollution data outputted by the indoor gas detection device A, making the controller module 45 control the on-off operation of the blower 1 and the wireless transmission of a target location. Moreover, the indoor gas detection device A receives the control command which is intelligently and selectively transmitted by the control central processor C through the intelligent computation and transmits the control command to the controller module 45 to perform filtering operation.

The driving movable module 46 is disposed in the main body 40 and electrically connected to the controller module 45 so as to be controlled by the controller module 45. The driving movable module 46 includes a plurality of rollable members 461 disposed on a bottom portion of the main body 40 and exposed to contact the ground, so that the rollable members 461 are controlled to drive the main body 40 to be moved.

The location checking unit 47 includes a plurality of location sensors disposed in the main body 40 and electrically connected to the controller module 45, wherein the location sensors are adapted to detect an obstacle outside the main body 40, to obtain a location information of the main body 40, and to transmit the location information of the main body 40 to the controller module 45 for processing and computation. In some embodiments, the location sensors may include an obstacle sensor which may be one of an infrared sensor, an ultrasonic sensor, or a radiofrequency identification sensor so as to detect a distance between the main body 40 and the obstacle to prevent the main body 40 from impacting the obstacle. In some embodiments, the location sensors may include a direct stream digital (DSD) sensor which is adapted to receive an external identification signal to detect the location of the main body 40 so as to generate and output the location information of the main body 40 and transmit the location information of the main body 40 to the controller module 45 for processing and computation. In some embodiments, the location sensors may include an inertia measurement sensor which may be a gyro sensor, an accelerator sensor, an earth inductor, or the like, so that the moving direction, the acceleration speeds along the transversal direction and the height direction, and the angular speed of the rolling, pitching, and yawing of the main body 40 thus can be obtained. The controller module 45 can calculate the speed and the heading angle of the rollable members 461 of the driving movable module 46 through integrating the acceleration speeds and angular speeds obtained by the inertia measurement sensor. In some embodiments, the location sensors may include a motor sensor for detecting the movement of the rollable members 461 of the driving movable module 46, so that the controller module 45 can perform compensation control to the rollable members 461 of the driving movable module 46 so as to change the rotational speeds of the rollable members 461. In some embodiments, the location sensors may include a cliff sensor so as to detect whether the main body 40 is in front of a cliff or a dead end.

As mentioned above, the controller module 45 is electrically connected to the indoor gas detection device A to receive the air pollution data output by the indoor gas detection device A, so that the controller module 45 processes and controls the on-off operation of the blower 1. Moreover, the controller module 45 receives the control command which is intelligently and selectively transmitted by the control central processor C through the intelligent computation and transmits the control command to the communication device 34 of the indoor gas detection device A for computation. The controller module 45 estimates a target track according to a residual distance between the target location and the location information of the main body 40, and together with the detection of the location sensors of the location checking unit 47, the controller module 45 controls the rollable members 461 of the driving movable module 46 to move toward the target track to allow the main body 40 to move toward the air pollution location, and the controller module 45 enables the blower 1 to perform cleaning and filtration at the air pollution location through the filtering component 2. Hence, the indoor gas detection device A together with the main body 40 on which the filtering component 2, the blower 1, the controller module 45, the driving movable module 46, and the location checking unit 47 are disposed form a movable filtering device B1, so that the air pollution in the indoor space can be cleaned and filtered instantly.

As aforementioned, according to one or some embodiments of the present invention, a system for detecting and cleaning indoor air pollution, adapted to be utilized in an indoor space with an HVAC system, is provided, wherein a plurality of gas detection devices is utilized to detect and identify a qualitative property, a concentration, and a location of an air pollution to output an air pollution data, wherein a plurality of filtering devices is utilized to filter the air pollution. After the gas detection device outputs the air pollution data, an intelligent computation is performed to determine the air pollution location, the gas detection devices transmit a control command intelligently and selectively to enable a filtering device closest to the air pollution location, therefore the air pollution can be guided to the filtering device closest to the air pollution location for rapidly filtering. Moreover, after the filtering devices receive the control command, a movable filtering device of the filtering devices is enabled to move toward the air pollution location. Moreover, filtering components of the filtering devices are utilized to filter the air pollution at the air pollution location and the air pollution outside the air pollution location which is diffused, moved, and directed by the air convection, accelerating the air pollution to be filtered, so that the air pollution of the indoor space is filtered to allow the indoor air pollution data of the indoor space to be lowered to the safety detection value, and the air of the indoor space is cleaned to a safe and breathable state. Hence, a performance of locating, guiding, cleaning and filtering the air pollution can be achieved.

The foregoing outlines features of several embodiments are proposed in the specification so that those skilled in the art may better understand the aspects of the present invention. Those skilled in the art should appreciate that they may readily use the present invention as a basis for designing or modifying other processes and structures for carrying out the same purposes and/or achieving the same advantages of the embodiments introduced herein. Those skilled in the art should also realize that such equivalent constructions do not depart from the spirit and scope of the present invention, and that they may make various changes, substitutions, and alterations herein without departing from the spirit and scope of the present invention.

What is claimed is:

1. A system for detecting and cleaning indoor air pollution, adapted to be utilized in an indoor space with heating, ventilation and air conditioning, wherein the system for detecting and cleaning indoor air pollution comprises:

at least one outdoor gas detection device configured to
detect a qualitative property and a concentration of an
air pollution of an outdoor air and output an outdoor air
pollution data;

a heating, ventilation and air conditioning system com-
prising a gate, at least one channel filtering member, a
flow-guiding device, and a plurality of channels,
wherein the channels are connected to the indoor space,
the gate controls the outdoor air to be introduced into
the heating, ventilation and air conditioning system, the
flow-guiding device guides the outdoor air introduced
into the channels to pass through and filtered by the at
least one channel filtering member, and the flow-
guiding device guides the filtered outdoor air into the
indoor space;

a plurality of indoor gas detection devices configured to
detect a qualitative property and a concentration of an
air pollution in the indoor space and output an indoor
air pollution data;

a plurality of filtering devices being physical-typed or
chemical-typed, wherein the filtering devices are dis-
posed in the indoor space, and each of the filtering
devices comprises at least one blower and at least one
filtering component; and a control central processor, wherein the control central
processor is configured to receive the outdoor air
pollution data detected by the at least one outdoor gas
detection device and the indoor air pollution data
detected by the indoor gas detection devices, perform-
ing a computation to locate an air pollution location of
the indoor space and transmit a control command
selectively, the control central processor is also con-
figured to control the gate to be opened or closed to
determine whether the outdoor air is introduced into the
indoor space through the at least one channel filtering
member after the control central processor performs the
computation;

wherein the at least one blower of each of the filtering
devices is driven by receiving the control command to
generate an air convection which is directed, so that the
air pollution in the indoor space is filtered to allow the
indoor air pollution data of the indoor space to be a
safety detection value, in which the air pollution data
approaches to a non-detection state, and the air in the
indoor space is cleaned to a safe and breathable state.

2. The system for detecting and cleaning indoor air
pollution according to claim 1, wherein the air pollution
comprises at least one selected from the group consisting of
particulate matters, carbon monoxide, carbon dioxide,
ozone, sulfur dioxide, nitrogen dioxide, lead, total volatile
organic compounds, formaldehyde, bacteria, fungi, viruses,
and any combination thereof.

3. The system for detecting and cleaning indoor air
pollution according to claim 1, wherein the at least one
flow-guiding device is a fan; each of the indoor gas detection
devices is disposed adjacent to a discharge port of a chamber
of a processing channel of a corresponding one of the
filtering devices, thereby each of the indoor gas detection
devices is configured to detect the qualitative property and
the concentration of the air pollution of the outdoor air
which is filtered by the corresponding one of the filtering
devices and discharged from the processing channel of the
corresponding one of the filtering devices; each of the
channels has a return inlet adapted to introduce the indoor air
in the indoor space back into the channels to be repeatedly
filtered.

4. The system for detecting and cleaning indoor air
pollution according to claim 1, wherein the at least one
channel filtering member is a high-efficiency particulate air
(HEPA) filter, a filter having a minimum efficiency reporting
value (MERV) 13 or higher, or any combination thereof.

5. The system for detecting and cleaning indoor air
pollution according to claim 1, wherein the safety detection
value comprises a detection value in which the air pollution
data approaches to the non-detection state.

6. The system for detecting and cleaning indoor air
pollution according to claim 5, wherein the safety detection
value includes at least one selected from the group consist-
ing of a concentration of PM2.5 which is less than 15 μg/m3,
a concentration of carbon dioxide (CO2) which is less than
1000 ppm, a concentration of total volatile organic com-
pounds (TVOC) which is less than 0.56 ppm, a concentra-
tion of formaldehyde (HCHO) which is less than 0.08 ppm,
a colony-forming unit per cubic meter of bacteria which is
less than 1500 CFU/m3, a colony-forming unit per cubic
meter of fungi which is less than 1000 CFU/m3, a concen-
tration of sulfur dioxide which is less than 0.075 ppm, a
concentration of nitrogen dioxide which is less than 0.1
ppm, a concentration of carbon monoxide which is less than
9 ppm, a concentration of ozone which is less than 0.06 ppm,
a concentration of lead which is less than 0.15 μg/m3, and
any combination thereof.

7. The system for detecting and cleaning indoor air
pollution according to claim 1, wherein the control central
processor is configured to receive the outdoor air pollution
data detected by the at least one outdoor gas detection device
and the indoor air pollution data detected by the indoor gas
detection devices to perform the computation, wherein the
computation performs artificial intelligent (AI) computation
and big data comparison to control the gate to be opened or
closed.

8. The system for detecting and cleaning indoor air
pollution according to claim 1, wherein the control central
processor is configured to receive the indoor air pollution
data detected by the indoor gas detection devices to perform
the computation, wherein the computation performs artifi-
cial intelligent (AI) computation and big data comparison to
locate the air pollution location in the indoor space and
transmit the control command selectively to the filtering
devices through wireless communication to drive the filter-
ing devices, thereby the air pollution is rapidly filtered by the
at least one filtering component.

9. The system for detecting and cleaning indoor air
pollution according to claim 8, wherein the computation
figures out a highest data among the indoor air pollution data
to determine the air pollution location in the indoor space,
the control command is selectively transmitted to a filtering
device at the air pollution location to enable the filtering
device, also, the control command is selectively transmitted
to rest of the filtering devices which are outside the air
pollution location to enable the rest of the filtering devices
to generate the air convection directed to the air pollution;
the air convection accelerates the filtration of the air pollu-
tion at the air pollution location and the air pollution outside
the air pollution location which is diffused, moved, and
directed by the air convection, and the filtering components
of the rest of the filtering devices outside the air pollution
location are enabled selectively, thus the air pollution in the
indoor space is filtered to allow the indoor air pollution data
of the indoor space to be lowered to the safety detection
value in which the air pollution data approaches to the
non-detection state, and the air in the indoor space is cleaned
to the safe and breathable state.

10. The system for detecting and cleaning indoor air pollution according to claim 8, wherein after the computation makes the comparison of the indoor air pollution data of the indoor space detected by at least three of the indoor gas detection devices, the indoor air pollution location in the indoor space is determined according to the indoor air pollution data detected by the at least three of the indoor gas detection devices through the computation, the control command is selectively transmitted to a filtering device nearby the air pollution location and a movable filtering device respectively, enabling the filtering device and the movable filtering device to move toward the air pollution location, thus accelerating the air pollution to be filtered by the filtering components of the filtering device and the movable filtering device at the air pollution location, also, the control command is selectively transmitted to rest of the filtering devices which are outside the air pollution location to enable the rest of the filtering devices to generate the air convection directed to the air pollution; the air convection accelerates the filtering of the air pollution at the air pollution location and the air pollution outside the air pollution location which is diffused, moved, and directed by the air convection, and the filtering components of the rest of the filtering devices outside the air pollution location are enabled selectively, therefore the air pollution in the indoor space is filtered to allow the indoor air pollution data of the indoor space to be lowered to the safety detection value in which the air pollution data approaches to the non-detection state, and the gas in the indoor space is cleaned to the safe and breathable state.

11. The system for detecting and cleaning indoor air pollution according to claim 1, wherein the filtering devices comprise a movable filtering device, the movable filtering device comprises a gas detection device, the gas detection device is configured to receive the control command to move toward the air pollution location, and a directional blower is capable of being moved upwardly and downwardly, as well as being rotated with respect to the movable filtering device to perform the air convection with a certain direction, thus accelerating the air pollution to be filtered by the filtering components of the filtering device and the at least one movable filtering device nearby the air pollution location, also, during the process that the at least one movable filtering device is moved to the air pollution location, the directional blower is enabled, and the control command is selectively transmitted to rest of the filtering devices which are outside the air pollution location to enable the rest of the filtering devices to generate the air convection directed to the air pollution; the air convection accelerates the filtering of the air pollution at the air pollution location and the air pollution outside the air pollution location which is diffused, moved, and directed by the air convection, and the filtering components of the rest of the filtering devices outside the air pollution location are enabled selectively, therefore the air pollution in the indoor space is filtered to allow the indoor air pollution data of the indoor space to be lowered to the safety detection value in which the air pollution data approaches to the non-detection state, and the gas in the indoor space is cleaned to the safe and breathable state.

12. The system for detecting and cleaning indoor air pollution according to claim 1, wherein the filtering devices comprises a physical type filtering device, the physical type filtering device comprises a filtering component, and the filtering component of the physical type filtering device filters the air pollution physically by a filter to block and absorb the air pollution.

13. The system for detecting and cleaning indoor air pollution according to claim 12, wherein the filter is a high-efficiency particulate air filter.

14. The system for detecting and cleaning indoor air pollution according to claim 1, wherein the filtering devices comprises a chemical type filtering device, the chemical type filtering device comprises a filtering component, and the filtering component of the chemical type filtering device filters the air pollution chemically by applying a degradation layer on the filtering component.

15. The system for detecting and cleaning indoor air pollution according to claim 14, wherein the degradation layer comprises at least one selected from the group consisting of an activated carbon, a cleansing factor layer having chlorine dioxide, an herbal protection coating layer including the extracts of *Rhus chinensis* Mill and the extracts of *Ginkgo biloba*, a layer of silver ions, a zeolite mesh, and any combination thereof.

16. The system for detecting and cleaning indoor air pollution according to claim 1, wherein the filtering devices comprises a chemical type filtering device, the chemical type filtering device comprises a filtering component, and the filtering component of the chemical type filtering device filters the air pollution chemically along with a light illumination.

17. The system for detecting and cleaning indoor air pollution according to claim 16, wherein the light illumination comprises at least one selected from the group consisting of a photocatalyst, a photocatalyst unit of an ultraviolet light, a photo plasma unit of a nanometer light tube, and any combination thereof.

18. The system for detecting and cleaning indoor air pollution according to claim 1, wherein the filtering devices comprises a chemical type filtering device, the chemical type filtering device comprises a filtering component, and the filtering component of the chemical type filtering device filters the air pollution chemically along with a degradation unit.

19. The system for detecting and cleaning indoor air pollution according to claim 18, wherein the degradation unit comprises at least one selected from the group consisting of a negative ion unit, a plasma ion unit, and any combination thereof.

20. The system for detecting and cleaning indoor air pollution according to claim 19, wherein the gas sensor comprises at least one selected from the group consisting of a volatile organic compound detector, a formaldehyde sensor, a bacterial sensor, a virus sensor, and any combination thereof; the volatile organic compound detector is capable of detecting information of carbon dioxide or total volatile organic compounds; the formaldehyde sensor is capable of detecting information of formaldehyde (HCHO) gas; the bacterial sensor is capable of detecting information of bacteria or fungi; the virus sensor is capable of detecting information of viruses.

21. The system for detecting and cleaning indoor air pollution according to claim 1, wherein each of the at least one outdoor gas detection device and the indoor gas detection devices is a gas detection device, the gas detection device comprises a control circuit board, a gas detection main body, a microprocessor, and a communication device; the gas detection main body, the microprocessor, and the communication device are integrally packaged and electrically connected to the control circuit board; the microprocessor controls the operation of the gas detection main body, the gas detection main body detects the air pollution and output a detection signal, and the microprocessor receives the detection signal to perform computation to generate the indoor air pollution data and the outdoor air pollution data and provides the indoor air pollution data and outdoor air pollution data to the communication device through a wireless transmission outwardly.

22. The system for detecting and cleaning indoor air pollution according to claim 21, wherein the gas detection main body comprises:

a base, having:
  a first surface;
  a second surface opposite to the first surface;
  a laser installation region hollowed out from the first surface to the second surface;
  a gas inlet groove recessed from the second surface and located adjacent to the laser installation region, wherein the gas inlet groove has a gas inlet through hole and two lateral walls; two light penetration windows penetrate on the two lateral walls of the gas inlet groove and are in communication with the laser installation region;
  a gas-guiding component installation region recessed from the second surface and in communication with the gas inlet groove, wherein a ventilation hole penetrates a bottom surface of the gas-guiding component installation region; and
  a gas outlet groove including a first region and a second region, wherein the first region is corresponding to the gas-guiding component installation region and is recessed from a portion of the first surface corresponding to a bottom surface of the gas-guiding component installation region; the second region is hollowed out from the first surface to the second surface in a region that is not corresponding to the gas-guiding component installation region; the gas outlet groove is in communication with the ventilation hole and has a gas outlet through hole;
a piezoelectric actuator received in the gas-guiding component installation region;
a driving circuit board covering and attached to the second surface of the base;
a laser component disposed on and electrically connected to the driving circuit board, wherein the laser component is received in the laser installation region, and a light path of a light beam emitted by the laser component passes through the light penetration windows and is orthogonal to the gas inlet groove;
a particulate sensor disposed on and electrically connected to the driving circuit board, wherein the particulate sensor is received in a position of the gas inlet groove where the path of the light beam emitted by the laser component is orthogonal to the gas inlet groove, so that the particulates in the air pollution passing through the gas inlet groove which is illuminated by the light beam of the laser component is detected by the particulate sensor;
a gas sensor disposed on and electrically connected to the driving circuit board, wherein the gas sensor is received in the gas outlet groove for detecting the air pollution introduced into the gas outlet groove; and
an outer cover covering the base and having a side plate, and the side plate has a gas inlet opening and a gas outlet opening, the gas inlet opening is corresponding to the gas inlet through hole of the base, and the gas outlet opening is corresponding to the gas outlet through hole of the base;
wherein when the outer cover is covered on the base and the driving circuit board is attached to the second surface of the base, a gas inlet path is defined by the gas inlet groove and a gas outlet path is defined by the gas outlet groove, thereby the piezoelectric actuator is driven to accelerate the introduction of the air pollution outside the gas inlet through hole into the gas inlet path defined by the gas inlet groove from the gas inlet opening; the air pollution passes through the particulate sensor to detect a particle concentration of the particulates contained in the air pollution; and the air pollution discharged into the gas outlet path defined by the gas outlet groove from the ventilation hole, detected by the gas sensor, and is discharged out of the gas detection main body from the gas outlet through hole and the gas outlet opening of the base.

23. The system for detecting and cleaning indoor air pollution according to claim 22, wherein the particulate sensor is capable of detecting particulate matters.

* * * * *